US008563009B2

(12) United States Patent
Agger et al.

(10) Patent No.: US 8,563,009 B2
(45) Date of Patent: Oct. 22, 2013

(54) USE OF MONOMYCOLYL GLYCEROL (MMG) AS AN ADJUVANT

(75) Inventors: Else Marie Agger, Copenhagen (DK); Claire Andersen, Bogliasco (IT); Peter Andersen, Brønshøj (DK); Gurdyal S. Besra, Solihull (GB); David E. Minnikin, Keswick (GB)

(73) Assignee: Statens Serum Institut, Copenhagen S (DK)

( * ) Notice: Subject to any disclaimer, the term of this patent is extended or adjusted under 35 U.S.C. 154(b) by 391 days.

(21) Appl. No.: 12/666,102

(22) PCT Filed: Jun. 26, 2008

(86) PCT No.: PCT/DK2008/000239
§ 371 (c)(1),
(2), (4) Date: Aug. 19, 2010

(87) PCT Pub. No.: WO2009/003474
PCT Pub. Date: Jan. 8, 2009

(65) Prior Publication Data
US 2010/0310585 A1    Dec. 9, 2010

(30) Foreign Application Priority Data
Jun. 29, 2007  (DK) ................................ 2007 00965

(51) Int. Cl.
*A61K 31/726*    (2006.01)
(52) U.S. Cl.
USPC ...................................................... 424/280.1
(58) Field of Classification Search
None
See application file for complete search history.

(56) References Cited

U.S. PATENT DOCUMENTS

| | | | |
|---|---|---|---|
| 4,243,663 | A | 1/1981 | Azuma et al. |
| 4,335,111 | A | 6/1982 | Lefrancier et al. |
| 5,955,077 | A | 9/1999 | Andersen et al. |
| 6,120,776 | A | 9/2000 | Hasløv et al. |
| 6,641,814 | B1 | 11/2003 | Andersen et al. |
| 6,649,170 | B1 | 11/2003 | Lindblad et al. |
| 6,982,085 | B2 | 1/2006 | Andersen et al. |
| 6,991,797 | B2 | 1/2006 | Andersen et al. |
| 7,037,510 | B2 | 5/2006 | Andersen et al. |
| 7,749,520 | B2 | 7/2010 | Davidsen et al. |
| 2002/0094336 | A1 | 7/2002 | Andersen et al. |
| 2003/0108527 | A1 | 6/2003 | Seya et al. |
| 2003/0235619 | A1 | 12/2003 | Allen et al. |
| 2004/0185057 | A1 | 9/2004 | Kirby et al. |
| 2005/0025710 | A1 | 2/2005 | Schneider et al. |
| 2005/0064595 | A1 | 3/2005 | MacLachlan et al. |
| 2005/0191308 | A1 | 9/2005 | Lindblad et al. |
| 2006/0008519 | A1 | 1/2006 | Davidsen et al. |
| 2008/0008724 | A1 | 1/2008 | Aagaard et al. |
| 2008/0267990 | A1 | 10/2008 | Andersen et al. |
| 2009/0186048 | A1 | 7/2009 | Aagaard et al. |
| 2010/0015171 | A1 | 1/2010 | Dietrich et al. |

FOREIGN PATENT DOCUMENTS

| | | |
|---|---|---|
| WO | WO 2005/004911 | 1/2005 |
| WO | WO 2006/002642 | 1/2006 |
| WO | WO/20060022642 A2 * | 12/2006 |

OTHER PUBLICATIONS

Silva (Brazilian Journal of Medical and Biological Research, vol. 18, No. 3, 1985, p. 327-335).*
Parant, et al., Nonspecific Immunostimulant Activities of Synthetic Trehalose-6,6'-Diesters (Lower Homologs of Cord Factor)m, Infection and Immunity, Apr. 1978, pp. 12-19, vol. 20, No. 1.
Agger, Pre-clinical evaluation and characterisation of adjuvant formulations in a novel subunit vaccine against *Mycobacterium tuberculosis*, Ph.D. thesis, Jun. 2006, The Department of Infectious Disease Immunology, Statens Serum Institut, XP002499006.
Andersen, et al., A simple Mycobacterial Monomycolated Glycerol Lipid Has Potent Immunostimulatory Activity, J. Immunol., 2009, pp. 424-432, vol. 182.
Andersen, et al., Novel Generation Mycobacterial Adjuvant Based on Liposome-Encapsulated Monomycolyl Glycerol from *Mycobacterium bovis* Bacillus Calmette-Guérin, J. Immunol., Jul. 20, 2009, pp. 1-9, vol. 183.
Barry III, et al., Mycolic Acids: Structure, Biosynthesis and Physiological Functions, Prog. Lipid Res., 1998, pp. 143-179, vol. 37, No. 2/3.
Bennekov, et al., Alteration of epitope recognition pattern in Ag85B and ESAT-6 has a profound influence on vaccine-induced protection against *Mycobacterium tuberculosis*, Eur. J. Immunol., 2006, pp. 3346-3355, vol. 36.
Bhowruth, et al., Adjuvant properties of a simplified C32 monomycolyl glycerol analogue, Bioorganic & Medicinal Chemistry Letters, Feb. 11, 2009, pp. 2029-2032, vol. 19.
Blum, et al., Improved silver staining of plaint proteins, RNA and DNA in polyacrylamide gels, Electrophoresis, 1987, pp. 93-99, vol. 8.
Brandt, et al., ESAT-6 Subunit Vaccination against *Mycobacterium tuberculosis*, Infection and Immunity, Feb. 2000, pp. 791-795, vol. 68, No. 2.
Brennan, et al., Structural Studies on the Type-specific Antigens and Lipids of the *Mycobacterium avium•Mybacterium intracellulare•Mycobacterium scrofulaceum* Serocomplex, J. Biol. Chem., May 25, 2009, pp. 4205-4211, vol. 254, No. 10.
Cheng, et al., Role of lipid trimming and CD1 groove size in cellular antigen presentation, The EMBO Journal, Jun. 22, 2006, pp. 2989-2999, vol. 25.

(Continued)

*Primary Examiner* — Brian J Gangle
(74) *Attorney, Agent, or Firm* — Howson & Howson LLP

(57) ABSTRACT

Here we identify MMG and its alpha- and ketomycolic acid derivatives as highly bioactive lipids derived from *M. bovis* BCG (Copenhagen) capable of stimulating and activating human DC's at exceedingly low doses. In addition to their direct role as immunostimulators of human DC's we demonstrate their use in the development of a new generation of adjuvants suitable for human administration. We furthermore identify a number of highly active synthetic MMG analogues with great potential in cancer treatment, and for vaccine adjuvants against both infectious disease and disorders like Alzheimers disease.

20 Claims, 11 Drawing Sheets

(56) References Cited

OTHER PUBLICATIONS

Figure 1:
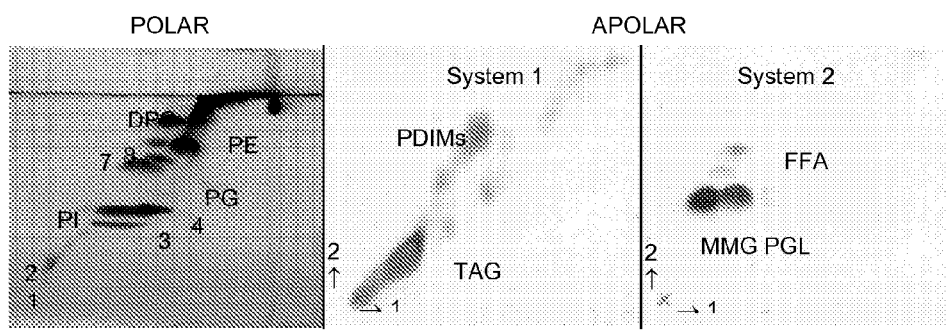
Figure 1:
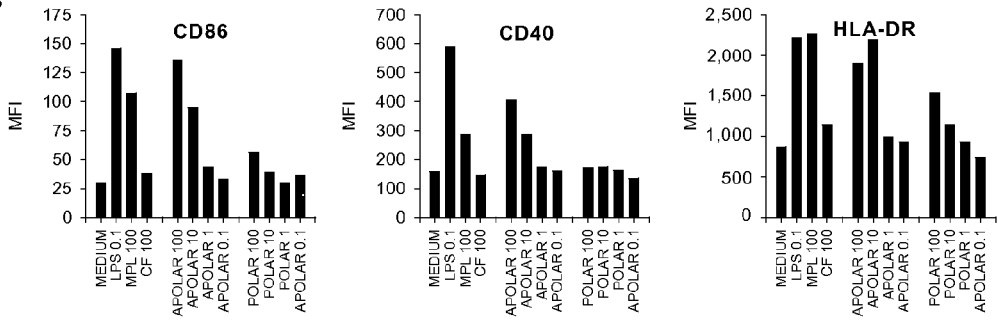
Figure 1:
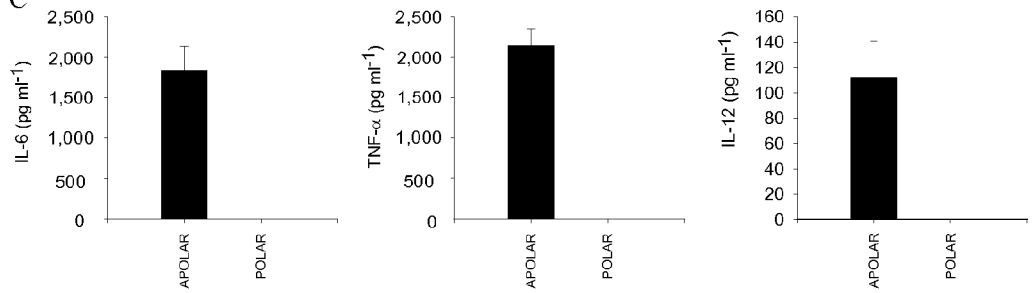
Figure 1:
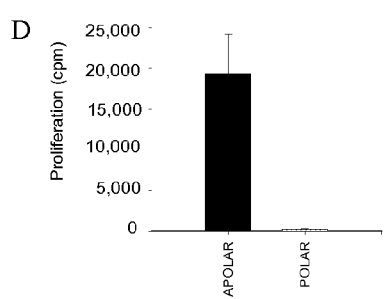
Figure 1:
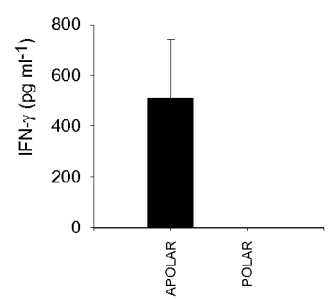

Cox, et al., Complex lipid determines tissue-specific replication of *Mycobacterium tuberculosis* in mice, Nature, Nov. 4, 1999, pp. 79-83, vol. 402.
Dascher, et al., Immunization with a mycobacterial lipid vaccine imprives pulmonary pathology in the guinea pig model of tuberculosis, International Immunology, 2003, pp. 915-925, vol. 15, No. 8.
Glück, Chapter 13: Liposonal Presentation of Antigens for Human Vaccines, Pharmaceutical biotechnology, 1995, pp. 325-345, vol. 6.
Gregoriadis, Engineering liposomes for drug delivery: progress and problems, Tibtech, Feb. 1995, pp. 527-537, vol. 13.
Gunstone, 13C-NMR studies of mono-, di- and tri-acylglycerols leading to qualitative and semiquantitative information about mixtures of these glycerol esters, Cheistry and Physics of Lipids, 1991, pp. 219-224, vol. 58.
Harboe, et al., B-Cell Epitopes and Quantification of the ESAT-6 Protein of *Mycobacterium tuberculosis*, Infection and Immunity, Feb. 1998, pp. 717-723, vol. 66, No. 2.
Hiu, Mycobacterial Adjuvant and its Carrier, Experimentia, Aug. 15, 1975, pp. 983-985, vol. 31, No. 8.
Indrigo, et al., Influence of trehalose 6,6'-dimycolate (TDM) during mycobacterial infection of bone marrow macrophages, Microbiology, 2002, pp. 1991-1998, vol. 148.
Koike, et al., Enhancing activity of mycobacterial cell-derived adjuvants on immunogenicity of recombinant human hepatitis B virus vaccine, Vaccine, 1998, pp. 1982-1989, vol. 16, No. 20.
Laemmli, et al., Cleavage of Structural Proteins during the Assembly of the Head of Bacteriophage T4, Nature, Aug. 15, 1970, pp. 680-685, vol. 227.
LeClerc, et al., Comparison of Immunomodulatory Activities in Mice and Guinea Pigs of a Synthetic Desmuramyl Peptidolipid Triglymyc, Infection and Immunity, Mar. 1984, pp. 870-875, vol. 43, No. 3.
Leech, et al., Preparation for Hapten Help by Glucan, Muramyl Dipeptide, and its L-ala-Glycerol-Mycolate Derivative, Journal of Leukocyte Biology, 1985, pp. 317-325, vol. 38.
Lima, et al., Role of Trehalose Dimycolate in Recruitment of Cells and Modulation of Production of Cytokines and NO in Tuberculosis, Infection and Immunity, Sep. 2001, pp. 5305-5312, vol. 69, No. 9.
Lindblad, et al., Adjuvant Modulation of Immune Responses to Tuberculosis Subunit Vaccines, Infection and Immunity, Feb. 1997, pp. 623-629, vol. 65, No. 2.
McBride, et al., Protective efficacy of a recombinant protective antigen against *Bacillus anthracis* challenge and assessment of immunological markers, Vaccine, 1998, pp. 810-817, vol. 16, No. 8.
Minnikin, et all., The Methyl-Branched Fortifications of *Mycobacterium tuberculosis*, Chemistry & Biology, May 2002, pp. 545-553, vol. 9.
Minnikin, I. Isolation and Purification of Mycobacterial Wall Lipids, Bacterial Cell Surface Techniques, 1988, pp. 125-135, Wiley.
Moingeon, et al., Towards the rational design of Th1 adjuvants, Vaccine, 2001, pp. 4363-4372, vol. 19.
Moody, et al., The molecular basis of CD1-mediated presentation of lipid antigens, Immunological Reviews, 1999, pp. 285-296, vol. 172.
Mosman, et al., The expanding universe of T-cell subsets: Th1, Th2 and more, Immunology Today, Mar. 1996, pp. 138-146, vol. 17, No. 3.
Nathan, et al., Identification of Interferon-γ as the Lymphokine That Activates Human Macrophage Oxidative Metabolism and Antimicrobial Activity, J. Exp. Med. Sep. 1, 1983, pp. 670-689, vol. 158.
Olsen, et al., Protection of Mice with a Tuberculosis Subunit Vaccine Based on a Fusion Protein of Antigen 85B and ESAT-6, Infection and Immunity, May 2001, pp. 2773-2778, vol. 69, No. 5.
Rao, et al., *Mycobacterium tuberculosis* controls host innate immune activation through cyclopropane modification of a glycolipid effective molecule, J. Exp. Med., Feb. 14, 2005, pp. 535-543, vol. 201, No. 4.
Reed, et al., A glycolipid of hypervirulent tuberculosis strains that inhibits the innate immune response, Nature, Sep. 2, 2004, pp. 84-87, vol. 431.
Romani, et al., Proliferating Dendritic Cell Progenitors in Human Blood, J. Exp. Med., Jul. 1, 1994, pp. 83-93, vol. 180.
Rosenkrands, et al., Cationic Liposomes Containing Mycobacterial Lipids: a New Powerful Th1 Adjuvant System, Infection and Immunity, Sep. 2005, pp. 5817-5826, vol. 79, No. 9.
Ryll, et al., Immunological Properties of Trehalose Dimycolate (Cord Factor) and Other Mycolic Acid-Containing Glycolipids—A Review, Microbiol. Immunol., 2001, pp. 801-811, vol. 45, No. 12.
Saito, et al., Adjuvant Effect of Cord Factor, a Mycobacterial Lipid, Infection and Immunity, Mar. 1976, pp. 776-781, vol. 13, No. 3.
Silva, Inflammation Induced by Mycolic Acid-Containing Glycolipids of *Mycobacterium bovis* (BCG), Brazilian J. Med. Biol. Res., 1985, pp. 327-335, vol. 18.
Sirakova, et al., The Largest Open Reading Frame (pks12) in the *Mycobacterium tuberculosis* Genome is Involved in Pathogenesis and Dimycocerosyl Phthiocerol Synthesis, Infection and Immunity, Jul. 2003, pp. 3794-3801.
Sprott, et al., Activation of Dendritic Cells by Liposomes Prepared from Phosphatidylinositol Mannosides from *Mycobacterium bovis* Bacillus Calmette-Guérin and Adjuvant Activity in Vivo, Infection and Immunity, Sep. 2004, pp. 5235-5246, vol. 72, No. 9.
Stanfield, et al., Single-Dose Antenatal Tetanus Immunisation, The Lancet, Feb. 3, 1973, pp. 215-219, vol. 1 (7797).
Suzuki, et al., Importance of Lyt 1+ T-Cells in the Antitumor Activity of an Immunomodulator, SSM, Extracted from Human-Type *Tubercle bacilli*, JNCI, Aug. 1986, pp. 441-447, vol. 77, No. 2.
Tsumita, et al., Studies on the Lipid of BCG, I. Glyceryl Mono-Mycolate in Wax C Fraction of the Lipid BCG, Jap. J. M. Sc. & Biol., 1956, pp. 205-216, vol. 9, No. 4-5.
Uehori, et al., Simultaneous Blocking of Human Toll-Like Receptors 2 and 4 Suppresses Myeloid Dendritic Cell Activation Induced by *Mycobacterium bovis* Bacillus Calmette-Guérin Peptidoglycan, Infection and Immunity, Aug. 2003, pp. 4238-4249, vol. 71, No. 8.
van Rooij, et al., Protective Antiviral Immune Responses to Pseudorabies Virus Induced by DNA Vaccination Using Dimethyldioctyadecylammonium Bromide as an Adjuvant, Journal of Virology, Oct. 2002, pp. 10540-10545, vol. 76, No. 20.
Yamazaki, Studies on the Allergenicity of Various Tuberculoprotein Derivatives and the Adjuvanticity of Wax D Fractions of *Mycobacterium tuberculosis*, Am. Rev. Respiratory Disease, 1969, pp. 691-698, vol. 100.
International Search Report and Written Opinion from International Stage of application (PCT/DK2008/000239) dated May 11, 2008.
Sep. 21, 2010 Examination Report in counterpart European Patent Application No. 08758248.2.
Feb. 18, 2011 Examination Report in counterpart European Patent Application No. 08758248.2.
Jul. 28, 2011 Examination Report in counterpart European Patent Application No. 08758248.2.
Oct. 17, 2011 Supplemental Response in counterpart European Patent Application No. 08758248.2.
Jan. 19, 2011 Response to Sep. 21, 2010 Examination Report in counterpart European Patent Application No. 08758248.2.
Jun. 8, 2011 Response to Feb. 18, 2011 Examination Report in counterpart European Patent Application No. 08758248.2.
Jul. 7, 2011 Corrective Response to Feb. 18, 2011 Examination Report in counterpart European Patent Application No. 08758248.2.
Aug. 24, 2011 Response to Jul. 28, 2011 Examination Report in counterpart European Patent Application No. 08758248.2.
Mar. 1, 2012 Notice of Intent to Grant in counterpart European Patent Application No. 08758248.2.
Mar. 1, 2012 Allowed claims in counterpart European Patent Application No. 08758248.2.

\* cited by examiner

A

B

Panel A

Panel B

A

B

USE OF MONOMYCOLYL GLYCEROL (MMG) AS AN ADJUVANT

CROSS-REFERENCE TO RELATED APPLICATIONS

This application is a national stage of International Patent Application No. PCT/DK2008/000239, filed Jun. 26, 2008.

FIELD OF INVENTION

The present invention discloses the use of monomycolyl glycerol (MMG), a synthetic homologue, analogue or modified version hereof for preparing an immunomodulator, an adjuvant, the adjuvant and a vaccine or a delivery system comprising this adjuvant.

GENERAL BACKGROUND

The first vaccines consisted of live, attenuated pathogens. The attenuated forms were either naturally occurring closely related organisms or obtained through serial passages in culture. For example, tuberculosis (TB) in man has for many years been combated by vaccination with an attenuated strain of *Mycobacterium bovis*, —the *M. bovis* BCG vaccine developed more than 80 years ago. However, although more than 3 billion doses of BCG have been administered (more than any other vaccine) it does not always provide satisfactory resistance to human TB in every population.

Today, a more up-to-date approach is to use highly purified substances, e.g. purified recombinant proteins or peptides. These vaccines are well-defined and side-reactions are minimized. Unfortunately, many highly purified substances are not very immunogenic and do not induce a sufficient immune response to confer protection. To do this, the antigen needs some help from immune response potentiating agents called adjuvants. Depending on the pathogen, protection may require that either a humoral or a cell-mediated response predominates. An immune reaction that can be transferred with immune serum is termed humoral immunity and refers to resistance that is mediated by antibodies which bind to antigenic material associated with an infectious agent and thereby trigger an immune response against it. Cell-mediated immunity (CMI) relies on the cells of the immune system mounting an immune response. A CMI, or T helper (Th)1, immune response is generally associated with combating intracellular pathogens, including Leishmania, and Tuberculosis, but also has a role in combating other types of infection e.g. the yeast infection Candida. A humoral, or Th2, immune response is required for defence against extracellular pathogens e.g. helminth infections.

In a number of cases e.g. Influenza, Hepatitis C (HCV), Human Immunodeficiency Virus (HIV), Chlamydia and Malaria depending on the stage of infection, a mixed Th1/Th2 response may be required (Mosmann and Sad 1996). These require both Th1 and Th2 because parts of their lifecycle are intracellular but they also go through extracellular phases e.g. transmission between cells.

The development of a specific kind of immune response (humoral or cell-mediated) can be determined by the choice of adjuvant. For example, protective immunity against intracellular pathogens like *M. tuberculosis* requires a cell-mediated immune response, and a suitable adjuvant for a subunit vaccine directed against TB should enhance a Th1 response (Lindblad et al. 1997).

A large number of adjuvants exist but most of these suffer from numerous problems that preclude their use in humans. Only a few adjuvants are accepted for human use e.g. aluminum-based adjuvants (AlOH-salts) and MF-59, but they both induce Th2-biased responses, which makes them unsuitable for a TB vaccine and other vaccines requiring a Th1 response (Lindblad et al. 1997).

During the past 20-30 years a number of new adjuvant systems have been identified and some of those are currently under development. Despite this, the need for new adjuvant systems is still recognized (Moingeon et al. 2001) and is evident in the paucity of choices available for clinical use.

An adjuvant (from latin adjuvare, to help) can be defined as any substance that when administered in the vaccine serves to direct, accelerate, prolong and/or enhance the specific immune response. Adjuvants has been divided into two major categories either delivery systems or immunomodulators/immunostimulators. The delivery system can e.g. be emulsions, polystyrene particles, niosomes, ISCOMS, virosomes, microspheres, or surfactant-like liposomes, which are vesicles made up of lipid bilayers. The liposomes act as carriers of the antigen (either within the vesicles or attached onto the surface) and may form a depot at the site of inoculation allowing slow, continuous release of antigen. For some time after injection and phagocytosis, liposomal presentation ensures that a specific amount of antigen is made available to single antigen-presenting cells (Gluck 1995). The immunomodulators targets distinct cells or receptor e.g. toll-like receptors on the surface of APCs. Delivery systems and immunomodulators can be used together e.g. as in Glaxo's series of adjuvants. Therefore, in addition to delivering the vaccine antigen delivery system can also be used for delivering the immunomodulators.

In addition to being a component in a vaccine, immunomodulators can be administered without antigen(s). By this approach it is possible to activate the immune system locally e.g. seen as maturation of antigen-presenting cells, cytokine production which is important for anti-tumor and anti-viral activity. Thus, the administration of immunomodulators may e.g. support in the eradication of cancer and skin diseases. Examples of immunomodulators which can be administered locally are Taxanes e.g. Taxol, the toll-like receptor 7/8 ligand Resiquimod, Imiquimod, Gardiquimod.

Dimethyldioctadecylammonium-bromide, -chloride, -phosphate, -acetate or other organic or inorganic salts (DDA) is a lipophilic quaternary ammonium compound, which forms cationic liposomes in aqueous solutions at temperatures above 40° C. DDA is a very efficient delivery system enhancing the uptake of vaccine antigen into APCs. Combinations of DDA and immunomodulating agents have been described. Administration of Arquad 2HT, which comprises DDA, in humans was promising and did not induce apparent side effects (Stanfield, 1973). The combination of DDA and TDB or DDA and MPL showed a very clear synergy between the delivery vehicle (DDA) and the immunomodulator (TDB or MPL) with highly elevated levels of CMI response compared to the response obtained with either components alone. DDA is therefore a promising delivery vehicle for vaccine antigen and an immunomodulator e.g. in the development of an adjuvant system for a vaccine against TB and other intracellular pathogens.

Various compounds from mycobacteria have been reported to be immunomodulating. When lipids extracted from *M. bovis* BCG were used as an adjuvant, a skin test response to ovalbumin was obtained in guinea pigs (Hiu 1975). Liposomes formed at elevated temperatures from total polar lipids of *M. bovis* BCG are able to generate a humoral response to ovalbumin, and a vaccine prepared from these polar lipids gave protection in mice upon challenge with tumor cells (WO 03/011336). The effect of total lipids from *M. tuberculosis* H37Rv as antigen in an experimental TB vaccine for guinea pigs was investigated by (Dascher et al. 2003). In this study, liposomes based on cholesterol and 1,2-distearoyl-sn-glycero-3-phosphocholine (DSPC) were mixed with a *M. tuberculosis* H37Rv total lipid extract. After removing the solvent, the lipids were reconstituted with dimethyldioctadecylammonium (DDA) as an adjuvant in PBS buffer. Guinea pigs immunised with this vaccine did not show a significant reduction in bacteria, suggesting that this formulation of liposomes mixed with DDA lacks a strong antigen or that the formulation of mycobacterial lipids with Cholesterol:DSPC prevent the adjuvanting effect of DDA. Alternatively, as a mixture of various lipids is administered, the effective lipids may constitute too limited a proportion of the total lipids.

Various purified components from mycobacteria have also been investigated for their adjuvant activity. Purified protein derivative (PPD) did not induce a delayed type hypersensitivity reaction on its own, but when Wax D (a mycobacterial cell wall peptidoglycan fragment-arabinogalactan-mycolic acid complex) was added as an adjuvant, a strong reaction was observed (Yamazaki S 1969). The immunomodulator SSM or Z-100, a lipid arabinomannan extracted from *M. tuberculosis*, has antitumor activity (Suzuki F 1986). Another mycobacterial cell-derived compound is trehalose 6,6'-dimycolate (TDM) (cord factor; a mycolic acid containing glycolipid) (Saito et al, 1976). Also, TDM (or synthetic analogues) has immunostimulatory effects and has been included in various adjuvant formulations (McBride et al. 1998) (Koike et al. 1998).

In a paper by Silva et al (1985), five components purified fra *Mycobacterium bovis* BCG was injected intravenously as lipid-coated charcoal particles and gave rise to an inflammatory reaction in the lungs of mice. The five components included TDM, trehalose monomycolate (MMT), glucose monomycolate (MMGlc), arabinose monomycolate (MMAr), and a glycerol monomycolate (MMGlyc). The paper describes the monomycolylglycerol headgroup whereas the composition of the mycolid acids is poorly defined and no structural data are provided. In addition, the reaction upon administration of the lipids is only described as an inflammatory activity in the lungs whereas the ability to enhance a specific immune response known as an adjuvant effect is not described.

Although the immunostimulatory and inflammatory activity of mycobacterial-derived lipids has been recognised for many decades with an ever-expanding literature of lipids capable of stimulating immune responses in animal (murine) models, to date individual lipid(s) with the ability to stimulate human dendritic cells (DCs) have not been identified. In example; although TDM has shown to be the most active mycobacterial lipid in terms of proinflammatory responses, no activation of dendritic cells upon stimulation with TDM has been observed (Uehori et al, 2003). So although TDM has shown inflammatory activity in several papers, this lipid apparently lacks the ability to activate the dendritic cells that are crucial for initiating an immune response. The identification of such a lipid with the ability to activate human dendritic cells would suggest that it could be used as part of a novel adjuvant system that would be suitable for use in humans. Furthermore, the lack of Th1-inducing adjuvants suitable for human use makes the identification of a single, mycobacteria-derived lipid with Th1-promoting capability a significant finding.

DCs are professional antigen presenting cells (APC) that play an essential role in directing the immune response upon infection with pathogens, such as *M. tuberculosis*. Hence, the production of IL-12 by activated DC represents a vital step in controlling *M. tuberculosis* infection since it is this cytokine that is of paramount importance in driving the production of IFN-γ by Th-1 cells, which promotes the activation of macrophages (Nathan et al. 1983). Furthermore, in recent years evidence has been uncovered that indicates that mycobacteria also target DC in an attempt to modulate the immune response and a crucial role for mycobacterial lipids in this process has been established.

Up to 40% of the dry weight of the cell envelope of mycobacteria is comprised of lipids (Minnikin 1982). These lipids have long been associated with the distinctive pathogenicity of this family of organisms and are known to play a substantial role in the host response to mycobacterial infection (Brennan and Goren 1979). Prominent among these lipids are the phthiocerol dimycocerosate (PDIM) waxes (Minnikin et al. 2002) the presence of which has been shown to correlate with pathogenicity; PDIM-deficient *M. tuberculosis* mutants show attenuated growth in mice (Sirakova et al. 2003). Closely related to the PDIMs are the so-called "phenolic glycolipids" (PGLs), a good example being the 2-methylrhamnosyl phenolphthiocerol dimycocerosates ("mycoside B") found in *Mycobacterium bovis*. A link between this monoglycosyl PGL and the hypervirulence of certain isolates of *M. tuberculosis* has recently been demonstrated (Reed et al. 2004).

Another lipid class of particular interest are the trehalose-6,6-dimycolates (TDM), the so-called "cord factors". TDM promotes the maintenance of granulomatous lesions by stimulating the release of pro-inflammatory cytokines, such as TNF-α, IL-6 and IL-12, and the Th-1-promoting cytokine IFN-γ (Lima et al. 2001) and has a role in prolonging the survival of *M. tuberculosis* inside macrophages by inhibiting phagosome-lysosome fusion (Indrigo et al. 2002). The fine structure of the mycolate components of TDM is important in the proinflammatory activation of macrophages during early infection (Rao et al, 2005).

Despite their role in enhancing mycobacterial survival, the immunomodulatory powers of mycobacterial lipids can also be harnessed to create a new generation of Th1-inducing adjuvants. In identifying individual lipids with potent immunostimulatory activity, it may be possible to circumvent the problems with toxicity associated with the use of heat-killed whole cells of *M. tuberculosis* mixed with oil—Freund's complete adjuvant (CFA)—while still maintaining the potent adjuvant activity. Indeed, liposomes formed from the polar lipids of *M. bovis Bacillus*-Calmette-Guerin (BCG) have recently been shown to activate murine bone marrow-derived dendritic cells (BM-DC). The majority of this activity was found to be attributable to the lipid glycophospholipid phosphatidylinositol dimannoside (Sprott et al. 2004).

Recent studies in our laboratories have characterised the novel adjuvant combination of a mycobacterial lipid extract from *M. bovis* BCG and dimethyldioctadecylammonium bromide (DDA) that is capable of promoting a complex and sustained immune response, with both a strong humoral and cell-mediated component (Rosenkrands et al. 2005). The majority of the adjuvant activity of the total BCG lipids was found to be attributable to the apolar lipids.

While these studies further confirm the potential of mycobacterial lipids to act as adjuvants, the optimal solution would be to identify the single most immunostimulatory lipid which, alone, has potent activity. This would represent an even simpler, cheaper adjuvant and would also raise the possibility of making synthetic analogues of the lipid allowing for a cleaner system that could be produced in the large quantities required of an adjuvant for use in vaccines that are administered worldwide.

SUMMARY OF THE INVENTION

The present invention discloses an immunostimulatory lipid, monomycolyl glycerol (MMG) and synthetic homologues, analogues and modified versions thereof, capable of activating human DCs. MMG is derived from the apolar fraction of the total BCG lipids and is responsible for inducing the adjuvant and protective effect associated with these lipids. Synthetic MMG with a smaller carbon backbone is capable of enhancing the stimulating properties of natural MMG on human DCs in vitro and also induces a strong Th1 response in vivo, which translates into a long lasting protective immune response against TB in the mouse model.

DETAILED DISCLOSURE OF THE INVENTION

The present invention discloses the use of monomycolyl glycerol (MMG) or synthetic homologues, analogues and modified versions thereof for preparing an immunomodulator, an adjuvant and a vaccine or a delivery system comprising this adjuvant which has a unique ability to stimulate human dendritic cells.

As immunomodulators MMG or synthetic homologues, analogues and modified versions thereof will be administered without antigen(s). By this approach it is possible to activate the immune system locally e.g. seen as maturation of antigen-presenting cells, cytokine production which is important for anti-tumor and anti-viral activity.

An adjuvant (from latin adjuvare, to help) can be defined as any substance that when administered in the vaccine serves to redirect, accelerate, prolong and/or enhance the specific immune response. Depending on the nature of the adjuvant it can promote a cell-mediated immune response, a humoral immune response or a mixture of the two. When used as a vaccine adjuvant an antigenic component is added to the adjuvant. Since the enhancement of the immune response mediated by adjuvants is non-specific, it is well understood in the field that the same adjuvant can be used with different antigens to promote responses against different targets e.g. with an antigen from M. tuberculosis to promote immunity against M. tuberculosis or with an antigen derived from a tumor, to promote immunity against tumors of that specific kind.

A preferred adjuvant disclosed by the invention is an adjuvant comprising MMG or a synthetic homologue, analogue or modified version thereof which further comprises a delivery vehicle e.g. emulsions, polystyrene particles, niosomes, ISCOMS, virosomes, microspheres, or surfactant-like liposomes. Preferred surfactants are most preferably cationic lipids based on dimethyldioctadecylammonium bromide or chloride (DDA-B or DDA-C) or the sulfate, phosphate or acetate salt hereof (DDA-X), or dimethyldioctadecenylammonium bromide or chloride (DODA-B or DODA-C) or the sulfate, phosphate or acetate compound hereof (DODA-X). Other types of preferred cationic lipids used in this invention include but are not limited to 1,2-dioleoyl-3-trimethylammonium propane (DOTAP), 1,2-dimyristoyl-3-trimethylammonium-propane, 1,2-dipalmitoyl-3-trimethylammonium-propane, 1,2-distearoyl-3-trimethylammonium-propane and dioleoyl-3-dimethylammonium propane (DODAP) and N-[1-(2,3-dioleyloxy)propyl]-N,N,N-trimethylammonium (DOTMA). Other surfactants are chosen among DXPC, DXPE, DXPG or combinations hereof where X is a replacement for the chainlength description e.g. P=palmitoyl (16C), S=stearoyl (18C), A=arachidoyl (20C).

The delivery vehicle may also be used for other immunomodulators such as TLR and non-TLR ligands like MPL (monophosphoryl lipid A), polyinosinic polycytidylic acid (poly-IC), muramyl dipeptide (MDP), zymosan, double-stranded RNA (dsRNA), DC-Chol, CpG oligodeoxynucleotides, cationic peptides, TDM, TDB, tamoxifen or any analogues of any of these molecules. Hence, a preferred adjuvant comprises MMG or a homologue, analogue or modified version thereof and further comprises a TLR- or non-TLR ligands in a delivery vehicle.

Delivery systems comprising MMG or synthetic homologues, analogues and modified versions thereof can be used for treating cancer, an autoimmune disorder, a nerve disorder e.g. Alzheimer, airway inflammation, inflammatory disorders, infectious disease, skin disorders, allergy, asthma or a disease caused by a pathogen. The MMG or synthetic homologues, analogues and modified versions thereof is administered in combination with one or more vaccines, antigens, antibodies, cytotoxic agents, allergens, antibiotics, antisense oligonucleotides, TLR- and non-TLR agonists, TLR- and non-TLR antagonists, peptides, proteins, gene therapy vectors, DNA vaccines or co-stimulatory molecules.

An antigenic component or substance is a molecule, which reacts with preformed antibody and/or the specific receptors on T and B cells. In the context of vaccination, a molecule that can stimulate the development of specific T or B cells, leading to the formation of a memory population of immune cells that will promote a faster "memory" response if the antigen is encountered a second time by immune cells. Since memory populations are rarely clonal, in practice this means that an antigen is any molecule or collection of molecules, which can stimulate an increase in immune responses when it is re-encountered by immune cells from an individual who has previously been exposed to it.

The invention further discloses a vaccine for parenterally, oral or mucosal administration or a delivery system comprising the adjuvant. A preferred vaccine comprises an antigenic epitope from an intracellular pathogen e.g. a virulent mycobacterium (e.g. the fusion products Ag85b_TB10.4, Ag85b_ESAT-6_Rv2660, Ag85b_TB10.4_Rv2660 and Ag85a_TB10.4_Rv2660), Plasmodium falciparum (Msp1, Msp2, Msp3, Ama1, GLURP, LSA1, LSA3 or CSP), Chlamydia trachomatis (e.g. CT184, CT521, CT443, CT520, CT521, CT375, CT583, CT603, CT610 or CT681), HIV, influenza or Hepatitis B or C. The adjuvant or delivery system can also be used in vaccines for treating cancer, allergy or autoimmune diseases.

A total mycobacterial lipid extract is a mixture of lipids obtained from a mycobacteria, e.g. BCG, M. microti, M. tuberculosis and M. vaccae, by a chemical or physical process. In the present work, the method used for extraction is the action of organic solvents (as described below), but other possibilities, known to those skilled in the art are possible.

The apolar lipid fraction is defined as non-polar lipids. The apolar lipid fraction is obtained by treating mycobacteria with a biphasic mixture of methanol/saline and petroleum ether. The petroleum ether extract is composed of apolar (non-polar) lipids. Hereafter, the polar lipid fraction is obtained by addition of chloroform to mycobacteria and the residual aqueous phase. The chloroform extract contains the remaining polar lipids. The major components in the apolar lipid fraction are phtiocerol dimycocerosates, triacylglycerols, trehalose mycolipenates and menaquinones. The major components of the polar lipid fraction are phospholipids such as phosphatidylethanolamine, phosphatidylglycerol, and phosphatidylinositol. Lipids of intermediate polarity are sulpholipids, trehalose mycolates, glycosylated phenolphthiocerols (including phenolic glycolipids, PGL's) and acylated trehaloses (Dobson et al, 1985).

MMG refers to the lipid monomycolyl glycerol obtained from the apolar lipid fraction, and derivatives e.g. alpha-MMG and keto-MMG and natural and synthetic analogues thereof. MMG can be isolated by TLCs run in toluene/acetone (95:5). PGL and MMG are extracted together by this method but can be separated on 1-D TLC in chloroform: methanol:0.880 ammonia (97:3:0.5). Derivatives of MMG, alpha-MMG and keto-MMG, can be obtained by heating overnight at 100° C. with 5% aqueous TBAH (2.5 ml) in a 16×100 mm tube (Minnikin 1988).

A synthetic homologue, analogue or modified version of MMG can be produced by any conventional method of chemical synthesis. An analogue refers to one of a group of compounds similar in structure but different in respect to elementary composition and homologue refers to any member of a homologues series of compounds. These compounds can be of varying carbon chain lengths; in particular a reduced size has been associated with reduced toxicity and may therefore serve to diminish any overt toxicity of the analogues. Hence, synthetic versions may be based on alkyl-chains with e.g. 8-36 carbons and with 0-3 double-bonds on each lipid tail. Alternatively, a simplified form can be obtained by removing one of the lipid tails. The carbon backbone size of the synthetic MMG is preferably C8-C36 e.g. 3-hydroxy-2-ethyl-hexanoic acid-2,3-dihydroxypropyl ester (C8), 3-hydroxy-2-butyl-octanoic acid-2,3-dihydroxypropyl ester (C12), 3-hydroxy-2-hexyl-decanoic acid-2,3-dihydroxypropyl ester (C16) 3-hydroxy-2-heptyl-undecanoic acid-2,3-dihydroxypropyl ester (C18), 3-hydroxy-2-tetradecyloctadecanoic acid-2,3-dihydroxypropyl ester (C32) or 3-hydroxy-2-hexadecylicosanoic acid-2,3-dihydroxypropyl ester (C36) and most preferably C8 or C16. Modified version can be prepared by replacing the glycerol moiety with other polyol head-groups e.g. polypropylene glycol and polyethylene glycerol. The stereochemistry around C2 and C3 of the synthetic monomycolate as well as in the glycerol can be varied. In the following MMG written alone also means a synthetic homologue, analogue or modified version of MMG as described above.

The antigenic component or substance can be a polypeptide or a part of the polypeptide, which elicits an immune response in an animal or a human being, and/or in a biological sample determined by any of the biological assays described herein. The immunogenic portion of a polypeptide may be a T-cell epitope or a B-cell epitope. In order to identify relevant T-cell epitopes which are recognized during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFN-gamma assay described herein. Another method utilizes overlapping oligopeptides (preferably synthetic having a length of e.g. 20 amino acid residues) derived from the polypeptide. These peptides can be tested in biological assays (e.g. the IFN-gamma assay as described herein) and some of these will give a positive response (and thereby be immunogenic) as evidence for the presence of a T cell epitope in the peptide. Linear B-cell epitopes can be determined by analyzing the B cell recognition to overlapping peptides covering the polypeptide of interest as e.g. described in Harboe et al, 1998.

Although the minimum length of a T-cell epitope has been shown to be at least 6 amino acids, it is normal that such epitopes are constituted of longer stretches of amino acids. Hence, it is preferred that the polypeptide fragment of the invention has a length of at least 7 amino acid residues, such as at least 8, at least 9, at least 10, at least 12, at least 14, at least 16, at least 18, at least 20, at least 22, at least 24, and at least 30 amino acid residues. Hence, in important embodiments of the inventive method, it is preferred that the polypeptide fragment has a length of at most 50 amino acid residues, such as at most 40, 35, 30, 25, and 20 amino acid residues. It is expected that the peptides having a length of between 10 and 20 amino acid residues will prove to be most efficient as diagnostic tools, and therefore especially preferred lengths of the polypeptide fragment used in the inventive method are 18, such as 15, 14, 13, 12 and even 11 amino acids.

Specifically the antigenic substance may be derived from a culture of metabolising *Mycobacterium tuberculosis*, *Mycobacterium bovis* and other environmental mycobacteria such as e.g. *Mycobacterium avium*. Particularly, interesting substances from the filtrate of such mycobacteria is the ESAT-6 gene family proteins (such as ESAT6 and TB 10.4) as well as other early antigens such as Ag85A, Ag85B, ORF2c, Rv1036 and Rv0285 which are dominant targets for cell mediated immunity in the early phase of tuberculosis in TB patients and in different animal models. Also other antigens such as Rv2653, Rv2655, Rv2656, Rv2657, Rv2658, Rv2659, Rv2660 which are dominant targets during later stages of TB infection are of relevance. Their immunogenecity per se is low, but in combination with the adjuvant combinations of the present invention it has turned out to be potent candidates for provoking high and persisting immunity against tuberculosis as is demonstrated in the following detailed part of this specification.

ESAT-6 gene family proteins as well as many other antigens applicable in combination with the adjuvant combinations of the present invention, today can be produced artificially, e.g. synthetically or by genetic recombinant techniques.

Fusion proteins has proven especially well suited as antigenic substances in vaccines e.g. the fusion products Ag85b_TB10.4, Ag85b_ESAT-6_Rv2660, Ag85b_TB10.4_Rv2660 and Ag85a_TB10.4_Rv2660 has proven very effective against TB.

A vaccine is defined as a suspension of dead, attenuated, or otherwise modified microorganisms (bacteria, viruses, or rickettsiae) or parts thereof for inoculation to produce immunity to a disease. The vaccine can be administered either prophylactic to prevent disease or as a therapeutic vaccine to combat already existing diseases such as cancer or latent infectious diseases but also in connection with allergy and autoimmune diseases. The vaccine can be emulsified in a suitable adjuvant for potentiating the immune response.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 µg to 1000 µg, such as in the range from about 1 µg to 300 µg, and especially in the range from about 1 µg to 50 µg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral or mucosal application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral or mucosal formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

The vaccine of choice can e.g. be:

Protein Vaccine: A vaccine composition comprising a polypeptide (or at least one immunogenic portion thereof) a peptide mixture or fusion polypeptide.

Live recombinant vaccines: Expression of the relevant antigen in a vaccine in a non-pathogenic microorganism or virus. Well-known examples of such microorganisms are *Mycobacterium bovis* BCG, Salmonella and Pseudomonas and examples of viruses are Vaccinia Virus and Adenovirus.

For all of these vaccine constructs, the addition of a suitable adjuvant has resulted in enhanced vaccine efficacies (Brandt et al, 2000), (van Rooij et al, 2002), (Bennekov et al, 2006).

Liposomes (or lipid vesicles) are aqueous compartments enclosed by a lipid bilayer. The lipid components are usually phospholipids or other amphiphiles such as surfactants, often supplemented with cholesterol and other charged lipids. Liposomes are able to entrap water- and lipid-soluble compounds thus allowing the liposome to act as a carrier. Liposomes have been used as delivery systems in pharmacology and medicine such as immunoadjuvants, treatment of infectious diseases and inflammations, cancer therapy, and gene therapy {Gregoriadis et al, 1995}. Factors which may have an influence on the adjuvant effect of the liposomes are liposomal size, lipid composition, and surface charge. Furthermore, antigen location (e.g., whether it is adsorbed or covalently coupled to the liposome surface or encapsulated in liposomal aqueous compartments) may also be important. Dendritic cells can be used as antigen delivery vehicles. Loading of antigen to antigen-presenting cells, such as dendritic cells, has shown to be an effective method for generating active T-cells with a role in antitumor immunity.

Quaternary ammonium compounds for example dimethyldioctadecylammonium-bromide, -chloride or other organic or inorganic salts hereof (DDA-B, DDA-C or DDA-X), dimethyldioctadecenylammonium chloride, -bromide or other organic or inorganic salts hereof (DODA-C, DODA-B or DODA-X), or 1,2-dioleoyl-3-trimethylammonium propane (DOTAP), 1,2-dimyristoyl-3-trimethylammonium-propane, 1,2-dipalmitoyl-3-trimethylammonium-propane, 1,2-distearoyl-3-trimethylammonium-propane and dioleoyl-3-dimethylammonium propane (DO-DAP) and N-[1-(2,3-dioleyloxy)propyl]-N,N,N-trimethylammonium (DOTMA) have the ability to form lipid aggregates such as lipid bilayers, liposomes of all types both unilamellar and multilamellar, micelles and the like when dispersed in aqueous medium. The lipid membranes of these structures provide an excellent matrix for the inclusion of other amphiphilic compounds such as glycolipids e.g. MMG or alpha,alpha'-trehalose 6,6'-dibehenate (TDB) which are shown to stabilize vesicle dispersions (Davidsen et al, PCT/DK2005/000467).

The combination of MMG and the delivery system can act in a synergistic way to enhance the immune response e.g. when DDA is administered alone. Hence, DDA promote low level of IFN-γ production, however in combination with MMG IFN-γ production is enhanced dramatically.

The liposomes of this invention can be made by a variety of methods well known in the art (Davidsen et al, PCT/DK2005/000467). The incorporation of MMG into liposomes/delivery systems can be made by a variety of methods well known in the art including simple mixing of liposomes and MMG. In particular, incorporation of MMG into liposomes can be made as described in Davidsen et al, PCT/DK2005/000467.

In addition to provide immunity to diseases the adjuvant combinations of the present invention can also be used for producing antibodies against compounds which are poor immunogenic substances per se and such antibodies can be used for the detection and quantification of the compounds in question, e.g. in medicine and analytical chemistry.

FIGURE LEGENDS

FIG. 1. Isolation and assessment of the immunostimulatory activity of apolar and polar lipids of *M. bovis* BCG. Polar and apolar lipids extracted from *M. bovis* BCG Copenhagen were analysed by 2-D TLC. In the polar lipid fraction, 1-4 are Phosphatidyinositol mannosides, PI is phosphatidylinositol, PE is phosphatidylethanolamine and DPG is diphosphatidylglycerol (cardiolipid). PG is L-alpha-phosphatidyl-DL-glycerol, while 5 and 6 are unknown phospholipids. In the apolar fraction TAG is triacylglycerol, PDIM is phthiocerol dimycocerosates A, B and C, MMG is monomycolyl glycerol, PGL is phenolic glycolipids and FFA are free fatty acids (Panel A). iDC were incubated for 24 h in the presence of medium alone, LPS (0.1 μg/ml), MPL (100 μg/ml), Cord Factor (CF) (100 μg/ml), apolar lipids (0.1-100 μg/ml) or polar lipids (0.1-100 μg/ml). The geometric mean fluorescent intensity (MFI) of levels of surface markers on DC following treatment are shown. Data obtained from one representative experiment of three using three different donors (panel B). Culture supernatants obtained following treatment with 100 μg/ml apolar or polar lipids were analysed by ELISA for the presence of the cytokines IL-6, TNF-α and IL-12. Data obtained from one representative experiment of three performed in triplicate, using three different donors, are presented (±s.e.m) (panel C). Proliferation (Panel D) and IFN-γ release (Panel E) by T cells from PPD-negative donors following incubation with DC treated for 24 hours with 100 μg/ml apolar or polar lipids in an MLR assay. Data obtained from one representative experiment of three performed in triplicate, using three different donors, are presented (±s.e.m).

FIG. 2. Structures of MMG, TAG, PDIM and PGL. 2-D TLC analysis of the individual lipids PDIM, TAG, PGL and MMG (Panel A) and representative structures of MMG, PGL, PDIMs and TAGs (Panel B).

FIG. 3. Activation of human dendritic cells by MMG. iDC were incubated for 24 h in the presence of medium alone (dotted line) or MMG, PDIM, PGL or TAG (10 μg/ml). The lipid preparations were found to be free of endotoxin contamination (<0.001 ng LPS/μg lipid). The MFI of the levels of surface markers on DC for one representative donor of six following treatment are shown (Panel A). Culture supernatants obtained following treatment with MMG, PDIM A, PGL or TAG (10 μg/ml) were analysed by ELISA for the presence of the cytokines IL-6, TNF-β and IL-12 (Panel B).

The mean (±s.e.m.) of data obtained from three or four experiment using different donors performed in triplicate are presented. Data was analysed using the Tukey test.

Figure 4:
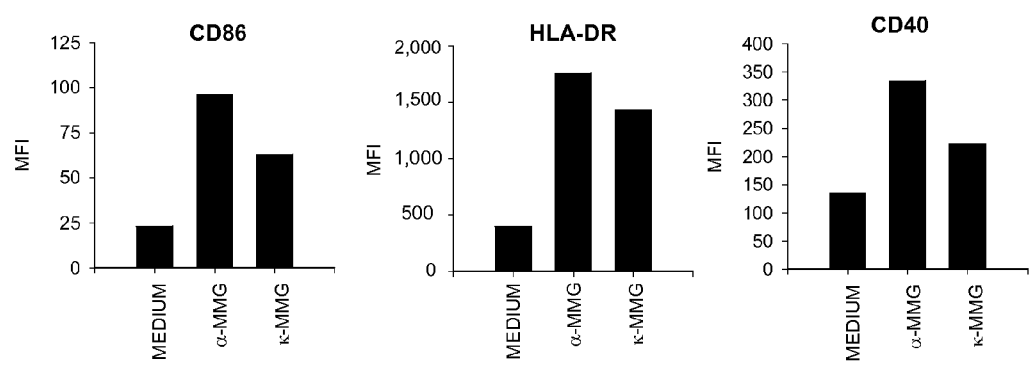

FIG. 4. Alpha- and ketomycolates of MMG are immunostimulatory. iDC were incubated for 24 h in the presence of medium alone and alpha- or ketomycolates of MMG (10 µg/ml). The MFI of surface markers on DC following treatment are shown.

Figure 5:
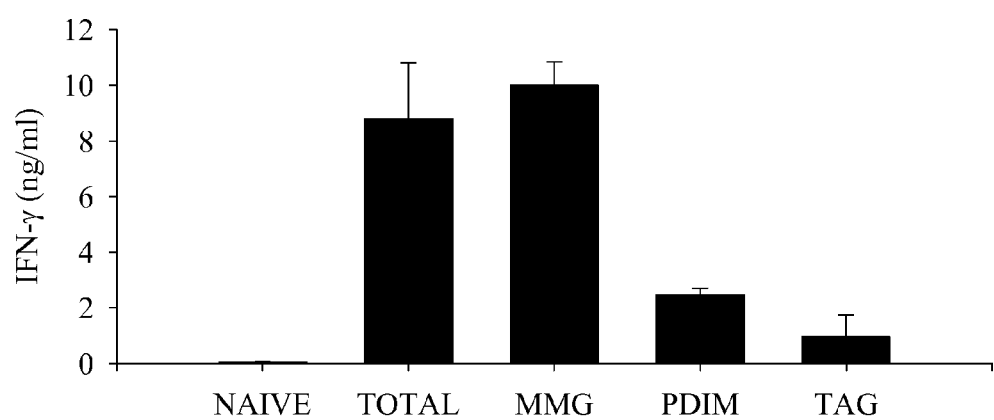

FIG. 5. IFN-γ release induced by MMG isolated from *M. bovis* BCG Copenhagen. C57BL/6 mice were immunised with Ag85B-ESAT-6 in combination with adjuvants based on lipids isolated from BCG Copenhagen incorporated into DDA liposomes. IFN-γ release by PBMC isolated from the draining lymph nodes days post vaccination weas measured.

Figure 6:
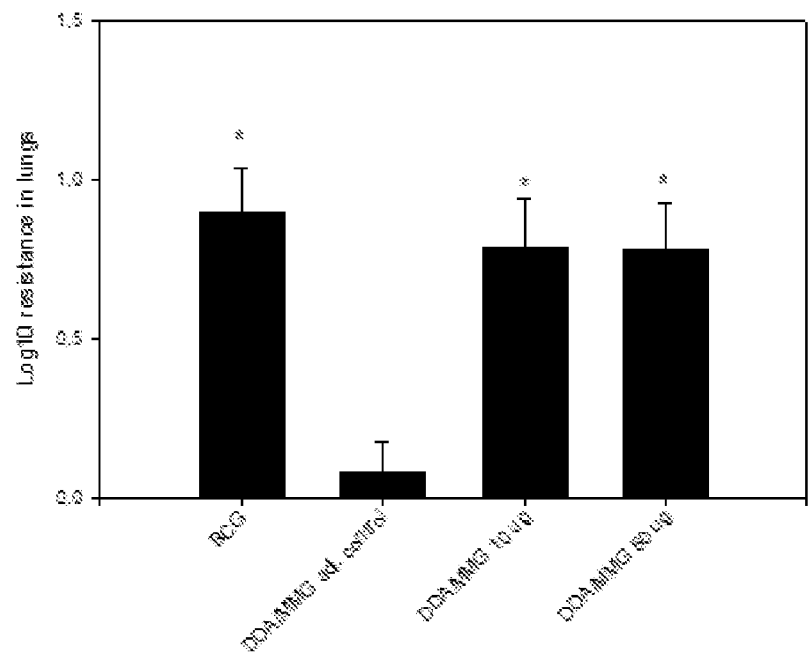
Figure 6:
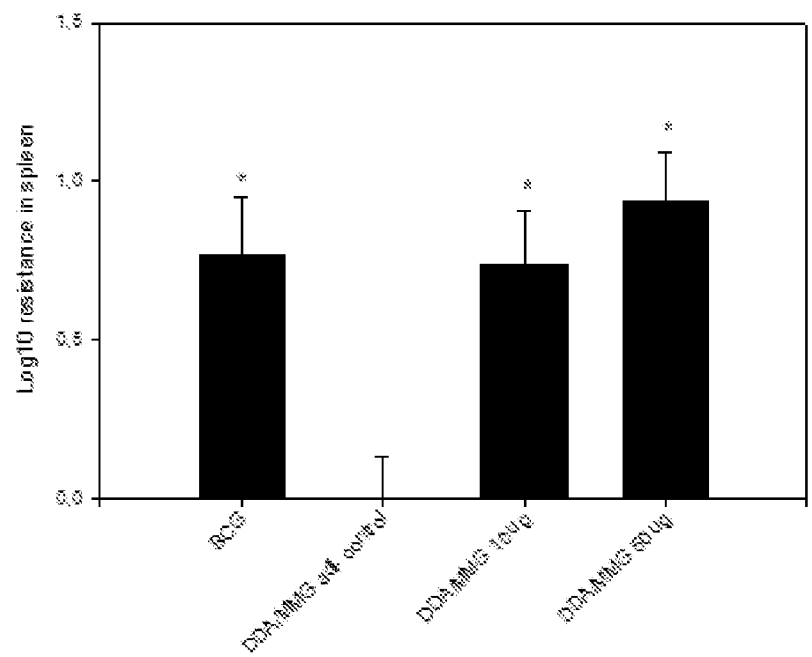

FIG. 6. Protection against a virulent TB infection with MMG adjuvants. C57BL/6 mice were immunised three times with Ag85B-ESAT-6 in combination with adjuvants based on DDA and 10 or 50 µg of MMG. Six weeks after the final vaccination, mice received an aerosol challenge with *M. tuberculosis*. Number of bacteria was measured in the lungs and spleen six weeks later. Mice receiving a standard BCG vaccination was included as a positive control and mice immunized with DDA/MMG (10 µg) without antigen as a negative control. The protective efficacy of the experimental vaccines is expressed as Log 10 reduction in bacterial load in the lung compared to unimmunized mice. Results are the mean values for six mice in each group±SEM. Values significantly different from the unimmunized control are marked *P<0.05.

Figure 7:
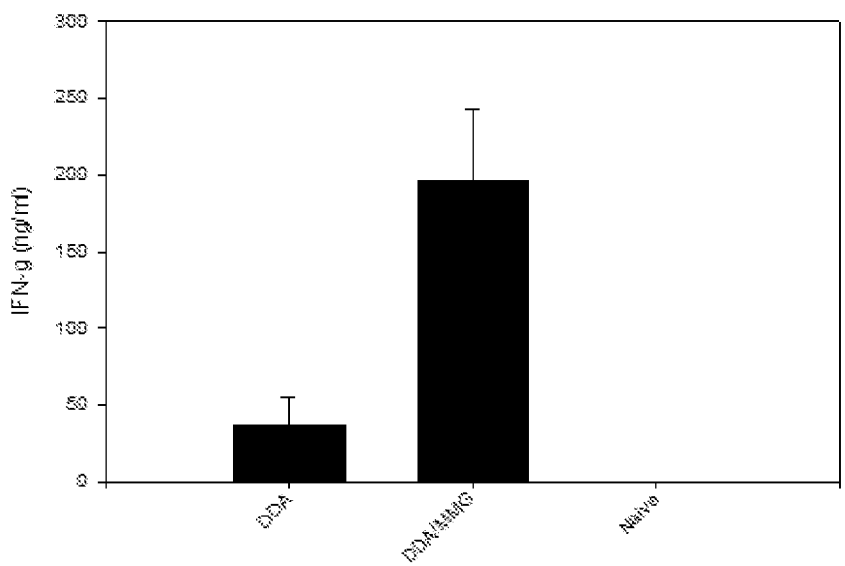
Figure 7:
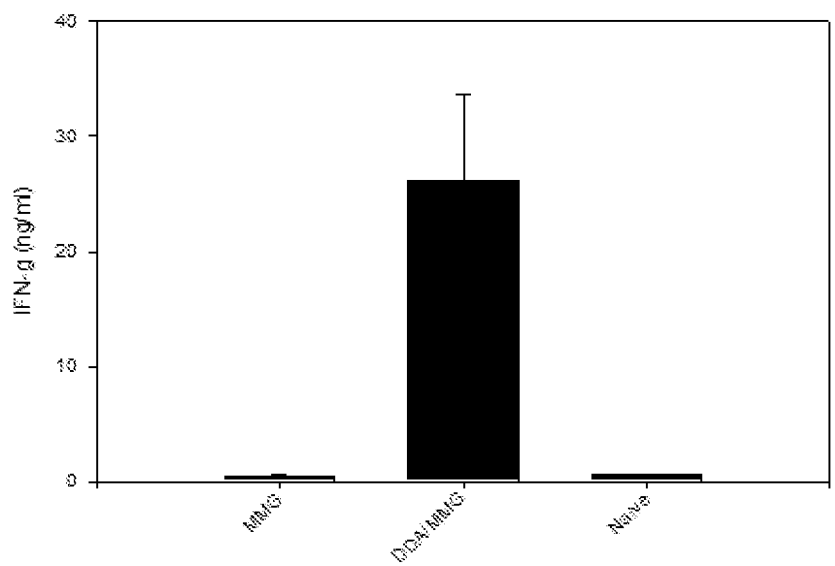

FIG. 7. IFN-γ release is enhanced by combining MMG and DDA. In two experiments, C57BL/6 mice were immunised with Ag85B-ESAT-6 in DDA or DDA/MMG (panel A) or MMG or DDA/MMG (panel B). IFN-γ release by PBMC isolated from the blood (panel A) or in spleens (panel B) 3 weeks after the last vaccination was measured.

Figure 8:
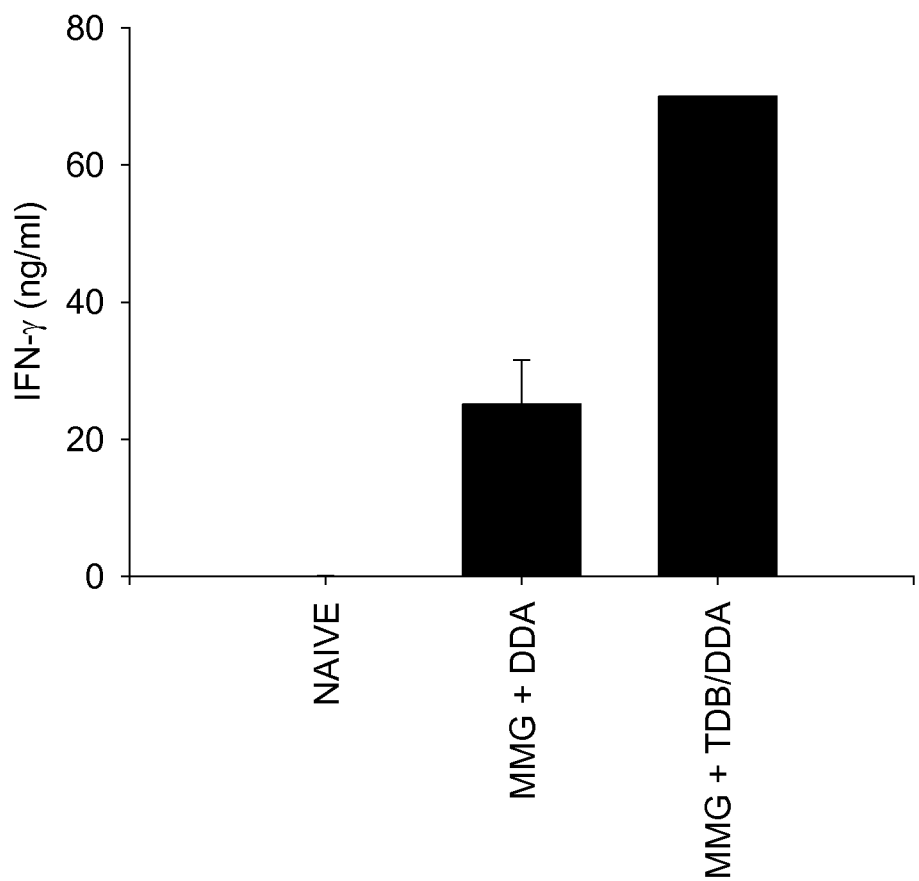

FIG. 8. IFN-γ release is enhanced by the addition of TDB to the MMG/DDA combination C57BL/6 mice were immunised with Ag85B-ESAT-6 administered in MMG incorporated into DDA liposomes or DDA liposomes containing TDB. IFN-γ release by PBMC isolated from the blood 5 months post vaccination was measured.

Figure 9:
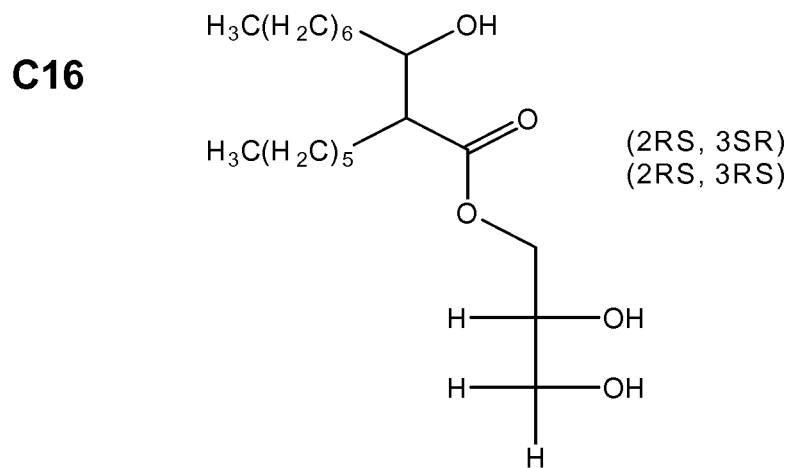
Figure 9:
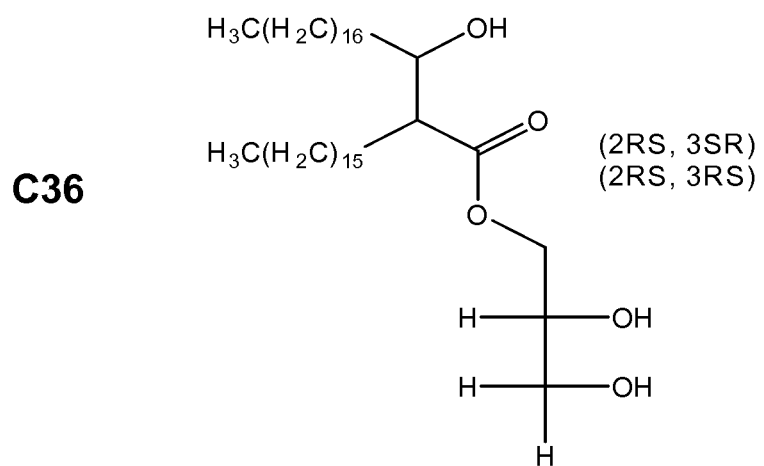

FIG. 9. Examples of structures of synthetic MMG analogues.

Figure 10:
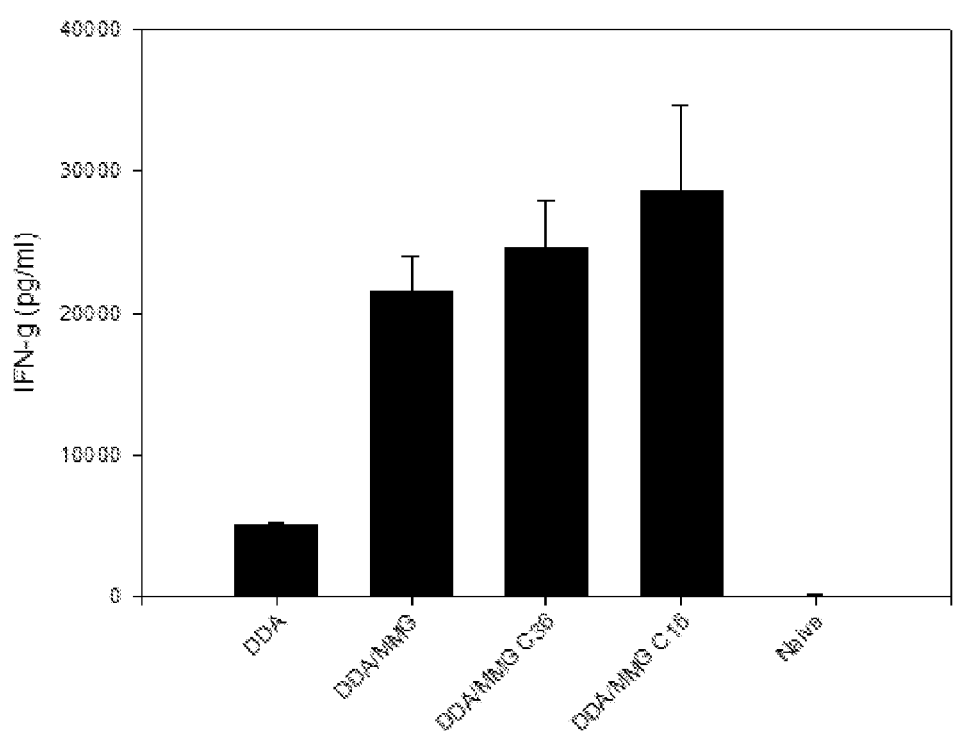

FIG. 10. Immune responses are comparable with natural and synthetic MMG analogues. C57BL/6 mice were immunised with Ag85B-ESAT-6 in DDA, DDA/MMG (10 DDA/MMG C36 (10 µg) or DDA/MMG C16 (10 µg). IFN-γ release by PBMC isolated from the blood one week after the last immunisation was measured.

Figure 11:
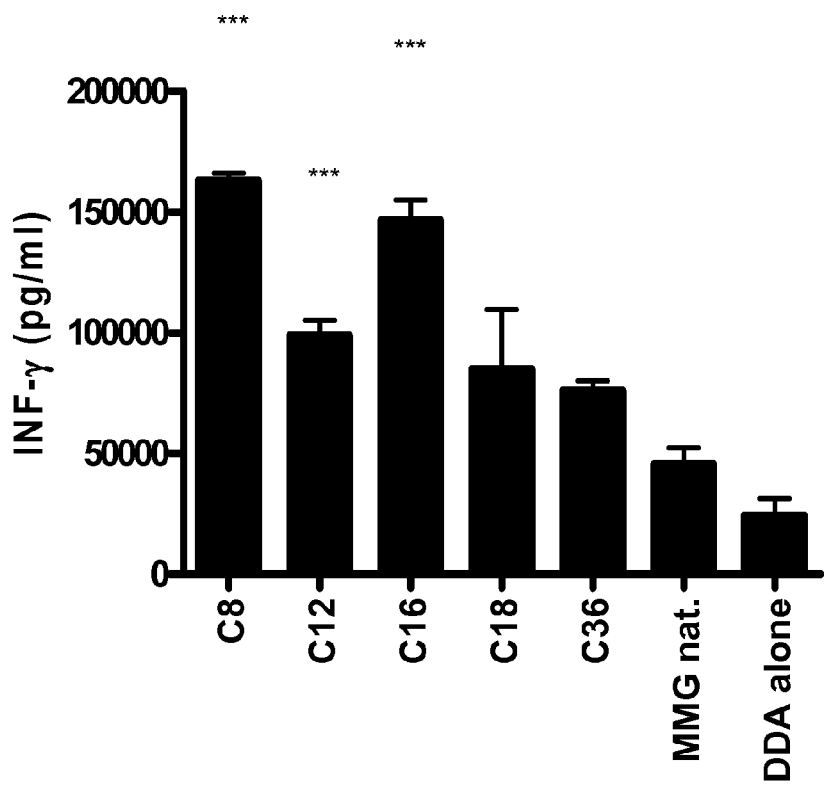

FIG. 11. Higher immune responses with shorter chain length. C57BL/6 mice were immunised with Ag85B-ESAT-6 in DDA or DDA with various MMG analgoues ranging from a chain length of 8 to 36 (1 µg/dose). IFN-γ release by PBMC isolated from the blood three weeks after the last immunisation was measured.

EXAMPLES

Material and Methods

Extraction of Apolar and Polar Lipids from *M. Bovis* BCG

*Mycobacterium bovis* BCG (Copenhagen) was cultured in modified Sauton medium. The mycobacteria were harvested after 2-3 weeks, suspended in PBS and killed by incubating for 1½ hours at 60° C. Apolar and polar lipids were extracted according to standard protocols (Dobson et al, 1985), (Rosenkrands et al, 2005).

For the extraction of apolar lipids, methanol:0.3% NaCl (440 ml) and 440 ml petroleum ether were added to 20 g of mycobacteria (wet weight) and the mixture stirred for 2 hrs. After centrifugation, the upper layer was removed and the lower layer was re-extracted with 440 ml petroleum ether. The supernatant phases from both extractions were pooled and evaporated to give apolar lipids.

For the extraction of polar lipids, the methanolic saline solution containing the biomass was heated in a boiling water bath for 10 mins at 100° C. followed by cooling for 10 mins at 37° C. A volume of 520 ml of chloroform:methanol:0-3% NaCl (9:10:3) was added and the mixture stirred overnight. The total mixture was passed through a sintered glass funnel; the filter cake was collected and re-extracted twice with 170 ml of chloroform:methanol:0-3% NaCl (5:10:4). All three aqueous methanolic chloroform phases were pooled and 580 ml chloroform:0.3% aqueous NaCl (1:1) added, with stirring, for 10 minutes. After allowing the phases to separate, the upper aqueous layer was removed and discarded. The lower organic layer was evaporated to dryness to provide polar lipids.

Purification of Individual Apolar Lipids

PDIMs and TAGs were isolated using TLCs run in petroleum ether/acetone (98:2); only the major component of PDIM, based on phthiocerol A, was recovered. PGL and MMG were isolated together by TLCs run in toluene/acetone (95:5). PGL and MMG were separated on 1-D TLC in chloroform:methanol:0.880 ammonia (97:3:0.5). The PDIMs, TAGs, PGL and MMG were subjected to 500 MHz $^1H$ and $^{13}C$ nuclear magnetic resonance (NMR) (Bruker drx500) and MALDI-TOF mass spectroscopy (MS) (Bruker Biflex IV). Samples (10 μl) of re-hydrated lipid extracts (1 mg/ml) were analysed by SDS-PAGE (Laemmli et al, 1970} and silver staining (Blum et al, 1987) for residual protein content. The lipid preparations were found to be free of endotoxin contamination (<0.001 ng LPS/μg lipid).

Hydrolysis of Monomycolyl Glycerol

Monomycolyl glycerol was heated overnight at 100° C. with 5% aqueous TBAH (2.5 ml) in a 16×100 mm tube (Minnikin et al, 1988). After cooling, the mixture was diluted with water (2 ml) and a 10% solution of iodomethane (3 ml) in dichloromethane was added and the tubes placed on a rotator for 1 h. The upper aqueous layer was discarded, the lower layer washed with equivolumes of 1M HCl and water and evaporated to dryness to yield a residue, shown by TLC (petroleum ether:acetone 95:5) to contain alpha- and keto mycolate methyl esters. Preparative TLC (as above) gave alpha methyl mycolate and keto methyl mycolate.

Trimethylsilyl derivatisation was used to separate alpha-MMG and keto-MMG. The MMG mixture and 600 ml of TRI-SIL reagent (Pierce) was heated at 75° C. for 20 min. The cooled solution was then dried under a stream of nitrogen and loaded onto a preparative-TLC plate and developed in petroleum-ether:toluene (50:50) and the alpha-MMG and keto-MMG bands visualized using 0.01% rhodamine and examined under long wave fluorescence. The corresponding bands were scraped from the TLC plate and the alpha-MMG and keto-MMG were extracted from the silica gel three times using diethyl-ether (3×5 mL). The pooled extracts were dried and the trimethylsilyl groups removed by the addition of heptane:methanol (1:1) and a few crystals of para-toluene sulfonic acid and mixed for 1 hr. The heptane layer was recovered and evaporated to dryness to afford purified alpha-MMG and keto-MMG.

Synthesis of MMG Showing Production of C36

3-Hydroxy-2-tetradecyl-octadecanoic acid (synthetic $C_{32}$ corynomycolic acid, synthesised according to Datta et al., 1991) (100 mg, 0.20 mmol, 1 eq) and 4-pyrrolidinopyridine (100 mg, 3 eq) was placed in a 50 ml round bottom flask and a solution of 50 μl 2,2-dimethyl-4-hydroxymethyl-1,3-dioxolan (sn-isopropylidene glycerol) in dichloromethane (500 μl) was added, along with 4 Å molecular sieves. The mixture was taken to complete dryness under high vacuum at room temperature and N',N-dicyclohexylcarbodiimidazole (DCC) (15 ml, 0.1 M DCC in DCM, 5 eq) was added and the reaction was left to stir at room temperature overnight. The molecular sieves were removed by filtration, the reaction mixture reduced to dryness in vacuo and the residue was purified using flash column chromatography (Fluka 60741 Silica Gel 60), eluting with hexane to hexane:ethyl acetate (8:2) in 5% increments to give the pure isopropylidene protected compound (3-hydroxy-2-tetradecyl-octadecanoic acid-2,2-dimethyl-[1,3]-dioxolan-4-ylmethyl ester) in 56% yield (68 mg). $^1$H NMR (CDCl$_3$, 300 MHz) $\delta_H$ 0.90 (t, 6H, CH$_3$), 1.20 (s, 54H, CH$_2$), 1.40 (s, 3H, CH$_3$), 1.45 (s, 3H, CH$_3$), 2.50 (m, 1H, CH), 4.05-4.40 (m, 5H, CH$_2$, CH); $^{13}$C NMR (CDCl$_3$, 75 MHz) $\delta_c$ 15.0 (CH$_3$), 22.1, 28.8, 28.9, 29.0, 31.4 (CH$_2$), 29.1 (CH$_3$), 52.1 (CH(CH$_2$)$_{13}$CH$_3$), 63.2 (CH$_2$OCO), 69.3 (CH$_2$O), 73.4 ($\overline{C}$H(CH$_2$)$_{14}$CH$_3$), 174.3 ($\overline{C}$=O); m/z (EI) 633.55 [M+Na$^+$] (100%); HRMS calcd for C$_{38}$H$_{74}$O$_5$Na [M+Na$^+$] 633.5536 found 633.5527.

3-Hydroxy-2-tetradecyl-octadecanoicacid-2,2-dimethyl-[1,3]-dioxolan-4-ylmethyl ester (68 mg, 1 eq) was dissolved in 6 ml of a trifluoroacetic acid: tetrahydrofuran:water (8:17:3, by vol.) solution and stirred at room temperature overnight. The solution was neutralised with saturated aqueous sodium bicarbonate and the mixture extracted twice with chloroform. The organic extract was washed with water and brine, dried and reduced in vacuo to yield the crude product as a white solid, which was purified by flash column chromatography on a 10 g silica gel Varian Bond Elut 12256026 cartridge, eluting with hexane to hexane:ethyl acetate (7:3) in 5% increments, to give the title compound as a white solid in 49% yield (32 mg). Melting point 72-74° C. $^1$H NMR (CDCl$_3$, 300 MHz) $\delta_H$ 0.90 (t, 6H, CH$_3$), 1.25 (s, 54H, CH$_2$), 2.50 (m, 1H, CH), 3.45-3.85 (m, 3H, CH, CH$_2$), 4.25 (m, 2H, CH$_2$); $^{13}$C NMR (CDCl$_3$, 75 MHz) $\delta_c$ 15.0 (CH$_3$), 26.3, 30.9, 31.3, 33.5 (CH$_2$), 47.5 (CH(CH$_2$)$_{13}$CH$_3$), 68.4 (CH$_2$), 69.5 (CH(CH$_2$)$_{14}$CH$_3$), 72.5 ($\overline{C}$H$_2$O), 76.4 (CH), 175.4 (C-1); $\overline{m}$/z (EI) 593.50 [M+Na$^+$] (100%); HRMS calcd for C$_{35}$H$_{70}$O$_5$Na [M+Na$^+$] 593.5121 found 593.5143.

Dendritic Cell Assays

Human PBMC-derived DCs were obtained according to a method modified from Romani et al., 1994. Peripheral blood was obtained from buffy coats. Briefly, monocytes were isolated by Ficoll-Hypaque centrifugation (Lymphoprep 1077 density medium, Nycomed, Oslo, Norway) followed by separation of CD14-positive cells using anti-CD14-labelled magnetic beads (MACS; Miltenyi Biotech, Bergesh Gladbach, Germany). The monocytes were cultured in complete RPMI 1640 supplemented with 10% FCS, 50 μM 2-mercaptoethanol, 100 U/ml penicillin, 100 μg/ml streptomycin, 2 mM L-glutamine (all Gibco) (CM) and in the presence of 100 ng/ml human recombinant GM-CSF (Prepotech, Rocky Hill, N.J., USA) and 50 ng/ml human recombinant IL-4 (Becton Dickinson (BD)) for 7 days at 37° C., 5% CO$_2$.

On Day 7 the iDC ($1\times10^5$ cells/ml) were cultured for a further 24 hours with Lipopolysaccharide (LPS) (*Escherichia coli* O127:B8) (Sigma-Aldrich, Brondby, Denmark) or *M. bovis* BCG-derived lipids. Lipid extracts were prepared by redissolving dry *M. bovis* lipid material with chloroform:methanol (2:1), followed by evaporation of the solvent and probe sonication into CM. Lipids were added to immature DC at 0.1 to 100 μg/ml.

Flow Cytometric Analysis

DCs were stained for surface markers by incubation first with the relevant mAb (BD Pharmingen) (30 min, 4° C.) followed by ½0 diluted FITC-conjugated goat anti-mouse Ig (Jackson ImmunoResearch Laboratories, West Grove, Pa.) (30 min, 4° C.). Non-specific Ab binding was blocked with 10% foetal calf serum solution (15 min, 4° C.) before addition of the relevant primary human mAb. The stained cells were examined by flow cytometry immediately, using a FACScan flow cytometer (BD) and analyzed with CellQuest software.

Cytokine Measurements

DC culture supernatants were collected and stored at −20° C. Secreted IL-12p70, IL-6 and TNF-α were measured by ELISA (BD) according to manufacturer's instructions.

Mixed Leucocyte Reaction (MLR) Assay iDC for the mixed lymphocyte reaction (MLR) assay were generated from monocytes as outlined above. The resultant cells were cultured for 24 hours in the same medium (iDC) or in the medium containing lipids (10 or 100 μg/ml). Titrations of DCs from $0.125\times10^5$ to $2\times10^5$ were incubated at 37° C./5% CO$_2$ with allogeneic T cells ($10^5$ cells/well) from a PPD-negative donor in flat-bottomed 96-well microtiter plates. T cells were isolated using a Pan-T cell isolation kit (Miltenyi) according to the manufacturer's instructions. The DC allogeneic T-cell cocultures were incubated for 6 days. The supernatant was harvested and stored at −20° C. until secreted IFN-γ was measured by ELISA (BD) according to manufacturer's instructions. Both assays were then pulsed with medium containing 1 μCi/well of [$^3$H] thymidine for the final 18 h of culture. Cells were harvested, and T-cell proliferation was measured by liquid scintillation counting (Microbeta Systems). All assays were performed in triplicate using at least three different donors.

Antigens

The fusion protein of Ag85B and ESAT-6 (in the following designated Ag85B-ESAT-6) was produced as recombinant proteins as previously described (Olsen et al, 2001).

Animals

Female BALB/c or C57BL/6 mice, 8 to 12 weeks old, were obtained from Bomholtgaard (Ry, Denmark) or Harlan Scandinavia (Denmark). Infected mice were kept in cages within a BL-3 laminar flow safety enclosure.

Immunisations

Mice were immunized subcutaneously (s.c.) at the base of the tails up to three times with a two week interval between each immunization. The vaccines (0.2 ml/mice) consisted of 2 μg of the fusion protein Ag85B-ESAT-6, emulsified in 250 μg DDA, and 10 μg rehydrated lipid extract, unless otherwise indicated. In some cases 11 mol % TDB was incorporated into DDA liposomes (Davidsen et al, PCT/DK2005/000467). As a positive control in the experiments involving *M. tuberculosis* infection, a single group of mice received one dose of BCG Danish 1331 injected subcutaneously at the base of the tail. Total or individual lipid extracts were prepared by rehydrating dry *M. bovis* lipid material with Milli Q water at 1 or 5 mg/ml followed by probe sonication. The standard lipid vaccines were prepared by mixing the antigen with saline, followed by addition of rehydrated lipid extract and DDA and vortex mixing. The vaccine was left over night to allow adsorption of the antigen.

Lymphocyte Cultures

Blood samples or inguinal lymph nodes were taken from mice 7-150 days after the last immunization and prepared as previously described (Rosenkrands et al, 2005). Cell cultures were performed in triplicate in round-bottomed microtiter wells containing $2\times10^5$ cells in a volume of 200 μl RPMI supplemented with 2-mercaptoethanol, glutamine, penicillin-streptomycin, hepes, and 10% foetal calf serum. Antigen for re-stimulation was used in a concentration of 5 μg/ml. Wells containing medium only or 5 μg/ml of ConA were included in all experiments as negative and positive controls, respectively. Culture supernatants were harvested from parallel cultures after 72 hours of incubation in the presence of antigen, and the amount of IFN-γ was determined by enzyme-linked immunosorbent assay (Brandt et al, 2000).

Experimental Infections

For evaluation of vaccine efficacy, mice were challenged 2.5 months after the first immunization by the aerosol route in a Glas-Col inhalation exposure system calibrated to deposit approx. 25 CFU of virulent *M. tuberculosis* Erdman in the lungs. The bacterial load in spleen and lungs were determined six weeks later by plating serial dilutions onto Middlebrook 7H11 agar supplemented with 2 μl 2-thiophenecarboxylic acid hydrazide per ml to selectively inhibit the growth of BCG. Colonies were counted after 2-3 weeks of incubation at 37° C.

Statistical Analyses

Differences in number of colonies between infected mice and control mice were tested by analysis of variance. When significant effects were indicated, differences between means were assessed by Dunnett's test. For human DC assays, differences in the release of cytokines in response to different lipids were tested by analysis of variance and when significant effects were indicated, difference between means were assessed by the Tukey test.

Example 1

Isolation and Immunostimulatory Activity of the Apolar Lipids from *M. Bovis* BCG The total lipids of *M. bovis* BCG was separated into polar and apolar fractions. In the polar fraction the lipids that could be identified were phosphatidylinositol mannosides (1-4), phosphatidylinositol (PI), phosphatidylethanolamine (PE), diphosphatidylglycerol (DPG) and L-alpha-phosphatidyl-DL-glycerol (PG). A number of unknown phospholipids were also identified (7 and 8) (FIG. 1A). In the apolar fraction the major lipids identified were phthiocerol dimycocerosates (PDIMs), triacyl glycerols (TAGs), phenolic glycolipid (PGL) and monomycolyl glycerol (MMG) (FIG. 1). FFA is free fatty acids.

Figure 2:
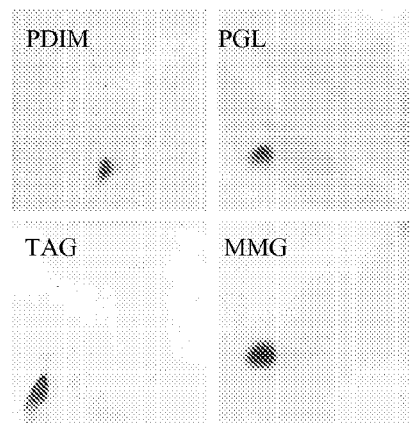
Figure 2:
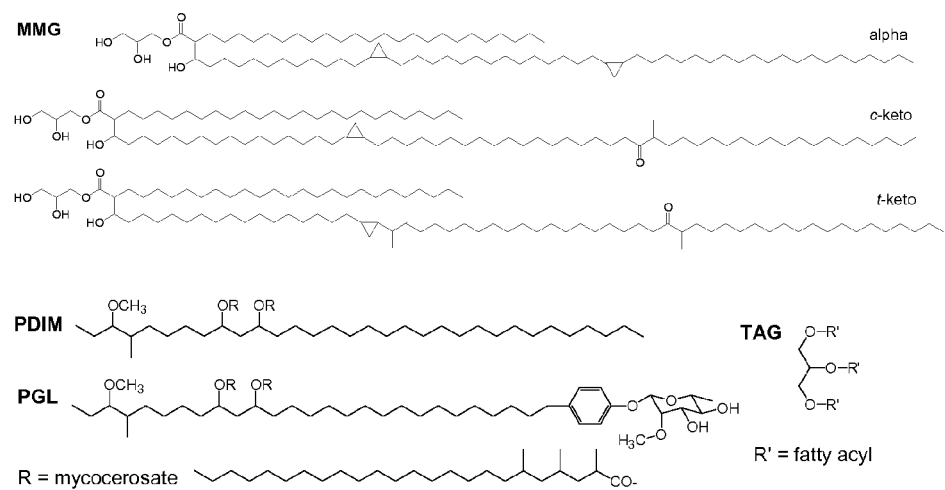

The comparative immunostimulatory activity of the apolar and polar lipids was examined using human peripheral blood monocyte-derived immature DC (iDC) (FIG. 1). Treatment with apolar lipids resulted in a dose-dependant elevation of the levels of the activation markers CD86, CD40 and HLA-DR as compared to untreated controls (FIG. 2B). A dose of 100 μg/ml apolar lipids resulted in DC activation comparable to that observed with the potent immunostimulatory molecule LPS (0.1 μg/ml) and superior compared to that of mycobacterial cord factor (TDM) and MPL. Up regulation of these molecules was accompanied by the secretion of the pro-inflammatory mediators tumour-necrosis factor-α (TNF-α), interleukin (IL)-6 and IL-12 (FIG. 2C). The levels of these pro-inflammatory cytokines in the supernatants of iDC treated with polar lipids were below the limits of detection using this assay. Finally, we used the mixed leucocyte reaction (MLR) using allogeneic T cells from a PPD-negative donor (FIGS. 2D & E), as another readout for DC activation. Further supporting the high activation state of DCs treated with the apolar lipids we found high levels of proliferation and IFN-γ release whereas no MLR was induced by the polar fraction.

Example 2

Isolation of Individual Lipids from the Apolar Lipid Extract of *M. Bovis* BCG and Characterisation of MMG Lipids from the immunostimulatory apolar fraction were isolated using preparative TLC to give pure samples of phthiocerol dimycocerosate A (PDIM A), TAGs, PGL and MMG; minor amounts of phthiocerol B and phthiodiolone A were also detected but were not recovered by the preparative methods employed (FIG. 2A). The structure and identities of the lipids were confirmed by $^1$H nuclear magnetic resonance (NMR) and mass spectroscopy (MS) (FIG. 2B and data not shown). The MMG component displayed $^1$H and $^{13}$C NMR spectra characteristic of a 1-monoacyl glycerol (Gunstone et al, 1991). MALDI-TOF MS coupled with the NMR data of the total MMG fraction (Table 1) revealed the presence of alpha-mycolate and keto-mycolate in the cis and trans form. The approximate ratio of the main components was 1.00:0.29:0.24, respectively.

TABLE 1

MALDI-TOF mass spectrometry of purified MMG.

| MMG c-keto | t-keto | α | CARBON NUMBER |
|---|---|---|---|
|  |  | 1206 | 79 |
|  |  | 1234 | 81 |
|  |  | 1262 | 83 |
| 1306 |  |  | 84 |
| 1335 |  |  | 86 |
|  | 1349 |  | 87 |
| 1363 |  |  | 88 |
|  | 1377 |  | 89 |
| 1391 |  |  | 90 |
|  | 1405 |  | 91 |

Signals are m/z for M + Na$^+$ ions. Major components of series are shown in bold with the main component underlined.

Example 3

Activation of Human Dendritic Cells by MMG

Figure 3:
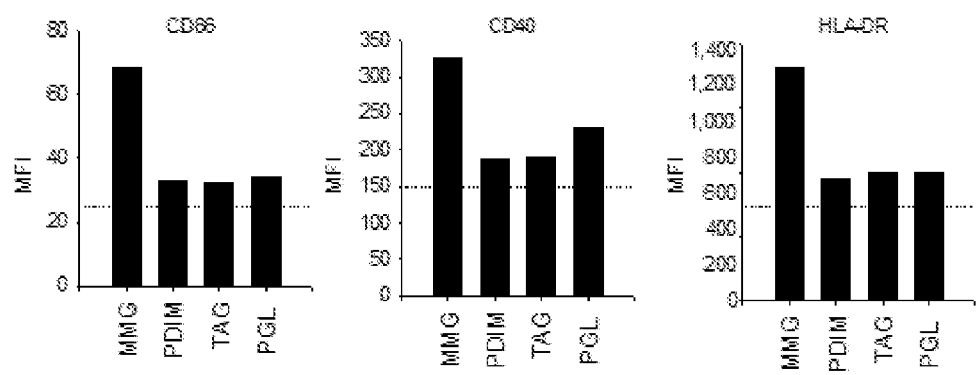
Figure 3:
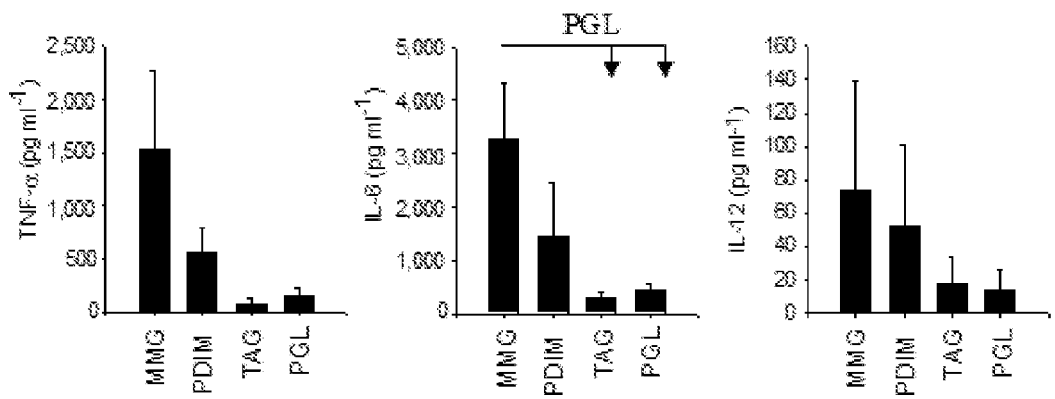

Purified MMG, PDIM A, PGL and TAGs were evaluated for their ability to activate human iDC. In these assays MMG was consistently found to be the most potent inducer of DC activation leading to a pronounced upregulation of CD86, CD40 and HLA-DR (FIG. 3A). MMG even activated DCs more than PDIM A, a lipid that has long been associated with the pathogenicity of Mycobacteria (Cox et al, 1999), that emerged as the second most active lipid, while PGL and TAGs induced less activation. In six individual donors the order of activation was observed as MMG>PDIM A>PGL>TAGs and the mean fold increase in CD86 levels above levels associated with untreated iDC were 1.91±0.29, 1.82±0.43, 1.52±0.26 and 1.32±0.14, respectively. Cytokine induction followed the same overall trend (FIG. 3B) with MMG standing out as the most potent immunostimulatory lipid. IL-6 was released by DC exposed to MMG at significantly greater levels (P<0.05) than that induced by PGL or TAG. No significant differences between cytokine inductions by the other lipids were recorded. MMG can therefore be classed as the most potent immunostimulatory lipid in the apolar lipid fraction of *M. bovis* BCG.

Example 4

Immunostimulatory Activity of Alpha- and Keto-MMG

In this example we wanted to further dissect the stimulatory properties of MMG and identify the active component responsible for its potent immunostimulatory capacity. The alpha-MMG and keto-MMG were separated following the preparation of trimethylsilyl ethers of MMG, preparative-TLC and subsequent hydrolysis of the trimethylsilyl ether protecting groups to afford alpha-MMG and keto-MMG. The structures of the alpha and keto-mycolates are documented in FIG. 2B. When assessed for their ability to activate human iDC, the alpha- and keto-MMG stimulated in the order of a 2-3-fold increase in the levels of activation markers (FIG. 4). Therefore the two sub-components of MMG also exhibit a marked ability to stimulate human DC.

Example 5

Induction of a Th1 Immune Response by MMG Isolated from *M. Bovis* BCG

In order to study the adjuvant activity of MMG, the isolated lipids were tested for their ability to induce IFN-γ production in mice. C57BL/6 mice were administered with 10 μg of total or individual lipids. In vivo, DDA serves as a vehicle in which to deliver the lipids. Therefore, 2 μg of the fusion protein Ag85B-ESAT-6 and 10 μg of rehydrated lipid extract, emulsified in 250 μg DDA, were administered by the subcutaneous route. A dose of 10 μg MMG incorporated into DDA liposomes resulted in IFN-γ levels of 10 ng/ml upon restimulation of PBMC isolated from the draining lymph node; a level that is comparable to that recorded for total lipids in DDA at the equivalent dose (FIG. 5). PDIM-A also induced IFN-γ production, albeit to a lower level, while DDA liposomes with TAG or PGL incorporated promoted very little IFN-γ release (FIG. 5 and data not shown). It should be noted that these individual lipids appear to be acting as adjuvants since no recall response upon restimulation with either a total lipid extract or the individual lipids was observed (data not shown). MMG was therefore identified as also being the most active apolar lipid in vivo, and alone could account for the majority of the adjuvant activity of BCG-derived total lipids.

Example 6

Protective Efficacy of MMG-Based Adjuvants

To evaluate the ability of MMG-based adjuvants to provide protection against a TB infection, C57BL/6 mice were immunized with Ag85B-ESAT-6 delivered in MMG (two different doses) and DDA. Groups of mice receiving a BCG vaccination and the adjuvant alone were included as positive and negative controls, respectively. Six weeks after the last vaccination, mice were challenged with live *M. tuberculosis* through the aerosol route. The ability of the vaccines to decrease bacterial load was measured in the lungs and spleen six weeks later. These data showed significant levels of protection with MMG/DDA as an adjuvant and protective levels comparable to that of BCG (FIG. 6). As expected this effect was specific as mice vaccinated with the adjuvant without antigen failed to inhibit bacterial growth.

Example 7

A Better Effect by Combining MMG and DDA

To evaluate the effect of combining an immunomodulators (MMG) and a delivery system (DDA), C57BL/6 mice were vaccinated with DDA alone or the combination of DDA/MMG (exp. 1, FIG. 7A) or in exp. 2 (FIG. 7B) with MMG alone or the combination of DDA/MMG. From these experiments it is clear that the immune response is enhanced dramatically by combining DDA and MMG.

Example 8

Enhancement of the Immune Response by Incorporation of TDB/Third Component into MMG and DDA Liposomes In order to study the effect on the adjuvant activity of MMG when combining with other immunostimulatory components, the immune response in C57BL/6 mice following subcutaneous immunisation with Ag85B-ESAT-6 and 10 μg MMG incorporated into DDA liposomes or DDA liposomes with the immunomodulators TDB incorporated {Davidsen et al, PCT/DK2005/000467} was assessed 5 months post first vaccination. While the combination of MMG incorporated into DDA liposomes resulted in IFN-γ levels of ~25 ng/ml upon restimulation of PBMC isolated from the blood, the release of IFN-γ was elevated dramatically when DDA liposomes with TDB incorporated were employed (FIG. 8). Therefore a synergistic effect was observed between MMG, DDA and TDB indicating that the addition of a third component to the MMG and DDA combination could further enhance the adjuvant activity.

Example 9

The Adjuvant Activity of MMG Analogues is Comparable to that of Natural MMG

To evaluate the immunological effect of synthetic MMG analogues, C57BL/6 mice were immunized with Ag85B-ESAT-6 in DDA with natural MMG, synthetic MMG analogue with 16 carbons (as depicted in FIG. 9) and synthetic MMG analogue with 36 carbons (as depicted in FIG. 9) (all 10 μg/DDA/MMG). The immune response was measured in the blood one week after the last vaccination and showed comparable levels of responses with the three MMG-based adjuvants whereas DDA on its own again showed a lower effect.

Example 10

Higher Immune Responses with Shorter Chain Length

To evaluate the immunological effect of synthetic MMG analogues with shorter chain lengths, C57BL/6 mice were immunized with Ag85B-ESAT-6 in DDDA alone, DDA with natural MMG, DDA with different synthetic analogues ranging from C8 to C36 (all 1 μg/dose). The immune response was measured in the blood three weeks after the last vaccination and demonstrated that synthetic MMG analogues are activate even at dose levels at 1 μg. Furthermore, these results also demonstrate that synthetic MMG analogues with shorter (from 16 C or less) are more effective compared to natural MMG. ***$P<0.001$. (FIG. 11)

REFERENCES

Bennekov, T., J. Dietrich, I. Rosenkrands, A. Stryhn, T. M. Doherty, and P. Andersen. 2006. Alteration of epitope recognition pattern in Ag85B and ESAT-6 has a profound influence on vaccine-induced protection against *Mycobacterium tuberculosis*. Eur. J. Immunol. 36(12): 3346-55.

Gregoriadis, G. 1995. Engineering liposomes for drug delivery: progress and problems. Trends Biotechnol. 13(12): 527-37.

Blum, H., H. Beier, and H. J. Gross. 1987. Improved silver staining of plant proteins, RNA and DNA in polyacrylamide gels. *Electrophoresis* 8: 93-99.

Brandt. L., M. Elhay, I. Rosenkrands, E. B. Lindblad, and P. Andersen. 2000. ESAT-6 subunit vaccination against *Mycobacterium tuberculosis*. Infect. Immun. 68: 791-795.

Brennan, P. J. and M. B. Goren. 1979. Structural studies on the type-specific antigens and lipids of the *mycobacterium avium. Mycobacterium intracellulare. Mycobacterium scrofulaceum* serocomplex. *Mycobacterium intracellulare* serotype 9. *J. Biol. Chem.* 254(10): 4205-4211.

Cox, J. S., B. Chen, M. McNeil, and W. R. Jacobs, Jr. 1999. Complex lipid determines tissue-specific replication of Mycobacterium tuberculosis in mice. *Nature* 402: 79-83.

Dascher, C. C., K. Hiromatsu, et al. 2003. Immunization with a mycobacterial lipid vaccine improves pulmonary pathology in the guinea pig model of tuberculosis. *Int. Immunol.* 15(8): 915-925.

Davidsen, J., Rosenkrands, I., and P. Andersen. (PCT/DK2005/000467)

Dobson, G., D. E. Minnikin, S. M. Minnikin, J. H. Parlett, M. Goodfellow, and M. Ridell, a. M. M. *Systematic analysis of complex mycobacterial lipids* (ed. Minnikin, M. G. a. D. E.) 237-265 (Academic Press, London, 1985).

Gluck, R. 1995. Liposomal presentation of antigens for human vaccines. *Pharm Biotechnol.* 6: 325-345.

Gunstone, F. D. 1991. *Chemistry and Physics of Lipids* 58: 219-224.

Harboe, M., A. S. Malin, H. S. Dockrell, H. G. Wiker, G. Ulvsund, A. Holm, M. C. Jørgensen, Andersen P. B-cell epitope and quantification of the ESAT-6 protein of *Mycobacterium tuberculosis*. Inft. Immun. 66(2):717-23.

Hiu, I. J. 1975. Mycobacterial adjuvant and its carrier. *Experientia.* 31(8): 983-5.

Indrigo, J., R. L. Hunter, Jr, et al. 2002. Influence of trehalose 6,6'-dimycolate (TDM) during mycobacterial infection of bone marrow macrophages. *Microbiology* 148(7): 1991-1998.

Koike, Y., Y. C. Yoo, et al. 1998. Enhancing activity of mycobacterial cell-derived adjuvants on immunogenicity of recombinant human hepatitis B virus vaccine. *Vaccine* 16(20): 1982-1989.

Laemmli, U. K. 1970. Cleavage of structural proteins during the assembly of the head of bacteriophage T4. *Nature* 227: 680-685.

Lima, V. M. F., V. L. D. Bonato, et al. 2001. Role of Trehalose Dimycolate in Recruitment of Cells and Modulation of Production of Cytokines and NO in Tuberculosis. *Infect. Immun.* 69(9): 5305-5312.

Lindblad, E., M. Elhay, et al. 1997. Adjuvant modulation of immune responses to tuberculosis subunit vaccines." *Infect. Immun.* 65(2): 623-629.

McBride, B. W., A. Mogg, et al. 1998. Protective efficacy of a recombinant protective antigen against *Bacillus anthracis* challenge and assessment of immunological markers. *Vaccine* 16(8): 810-817.

Minnikin, D. E. 1982. Lipids: complex lipids, their chemistry, biosynthesis and roles. *The Biology of the Mycobacteria.* C. R. a. J. L. Stanford. London, Academic Press.

Minnikin, D. E. in *Bacterial Cell Surface Techniques* (ed. Hancock, I. C., Poxton, I. R.) 125-135 (Wiley, Chichester, 1988).

Minnikin, D. E. 1988. Isolation and purification of mycobacterial wall lipids. *Bacterial Cell Surface Techniques*. I. C. Hancock, Poxton, I. R. Chichester, Wiley: 125-135.

Minnikin, D. E., L. Kremer, et al. 2002. "The Methyl-Branched Fortifications of Mycobacterium tuberculosis. *Chemistry & Biology* 9(5): 545-553.

Moingeon, P., J. Haensler, et al. 2001. Towards the rational design of Th1 adjuvants. *Vaccine* 19(31): 4363-4372.

Mosmann, T. R. and S. Sad 1996. The expanding universe of T-cell subsets: Th1, Th2 and more. *Immunology Today* 17(3): 138-146.

Nathan, C., H. Murray, et al. 1983. Identification of interferon-gamma as the lymphokine that activates human macrophage oxidative metabolism and antimicrobial activity. *J. Exp. Med.* 158(3): 670-689.

Olsen, A. W., L. A. H. van Pinxteren, L. M. Okkels, P. B. Rasmussen, and P. Andersen. 2001. Protection of Mice with a Tuberculosis Subunit Vaccine Based on a Fusion Protein of Antigen 85B and ESAT-6. Infect. Immun. 69:2773-2778.

Rao V, F. N., Porcelli S A, Glickman M S 2005. *Mycobacterium tuberculosis* controls host innate immune activation through cyclopropane modification of a glycolipid effector molecule. *J Exp Med* 201: 535-543.

Reed, M. B., P. Domenech, et al. 2004. A glycolipid of hypervirulent tuberculosis strains that inhibits the innate immune response. *Nature* 431(7004): 84-87.

Romani, N., S. Gruner, D. Brang, E. Kampgen, A. Lenz, B. Trockenbacher, G. Konwalinker, P. O. Fritsch, R. M. Steinman, and G. Schuler. 1994. Proliferating dendritic cell progenitors in human blood. *J. Exp. Med.* 180: 83-93.

Rosenkrands, I., E. M. Agger, A. W. Olsen, K. S. Korsholm, C. S. Andersen, K. T. Jensen, and P. Andersen. 2005. Cationic Liposomes Containing Mycobacterial Lipids: a New Powerful Th1 Adjuvant System. *Infect. Immun.* 73: 5817-5826.

Saito, R., Tanaka, A., Sugiyama, K., Azuma, I. and Yamamura, Y. 1976. Adjuvant effect of cord factor, a mycobacterial lipid." *Infect Immun.* 13(3): 776-781.

Silva, C. L. 1985. Inflamation induced by mycolic acid-containing glycolipids of *Mycobacterium bovis* (BCG). *Brazilian J. Med. Biol. Res.* 18: 327-335.

Sirakova, T. D., V. S. Dubey, et al. 2003. The Largest Open Reading Frame (pks12) in the Mycobacterium tuberculosis Genome Is Involved in Pathogenesis and Dimycocerosyl Phthiocerol Synthesis. *Infect. Immun.* 71(7): 3794-3801.

Sprott, G. D., C. J. Dicaire, et al. 2004. Activation of Dendritic Cells by Liposomes Prepared from Phosphatidylinositol Mannosides from *Mycobacterium bovis Bacillus* Calmette-Guerin and Adjuvant Activity In Vivo. *Infect. Immun.* 72(9): 5235-5246.

Stanfield, J. P., D. Gall, Bracken P. M. 1973. Single-dose antenatal tetanus immunisation. Lancet 1(7797):215-9.

Suzuki F, B. R., Pollard R B. 1986. Importance of Lyt 1+ T-cells in the antitumor activity of an immunomodulator, SSM, extracted from human-type *Tubercle bacilli.* 1986 77(2): 441-7.

Uehori, J., M. Matsumoto, S. Tsuji, T. Akazawa, O. Takeuchi, S. Akira, T. Kawata, I. Azuma, K. Toyoshima, and T. Seya. 2003. Simultaneous blocking of human Toll-like receptors 2 and 4 suppresses myeloid dendritic cell activation induced by *Mycobacterium bovis Bacillus* Calmette-Guerin peptidoglycan. *Infect. Immun.* 71:4238-4249.

van Rooij, E. M. A., H. L. Glansbeek, et al. 2002. Protective Antiviral Immune Responses to Pseudorabies Virus Induced by DNA Vaccination Using Dimethyldioctadecylammonium Bromide as an Adjuvant." *J. Virol.* 76(20): 10540-10545.

Yamazaki S, K. K., Someya S, Azuma I, Yamamura Y. 1969. Studies on the allergenicity of various tuberculoprotein derivatives and the adjuvanticity of wax D fractions of *Mycobacterium tuberculosis. Am Rev Respir Dis.* 100(5): 691-8.

The invention claimed is:

1. A synthetic monomycolyl glycerol compound comprising a monomycolyl group and a glycerol group, wherein said monomycolyl group comprises a backbone, said backbone consisting of 8 to 36 carbon atoms.

2. The synthetic monomycolyl glycerol compound according to claim 1, wherein said backbone consists of 8 to 16 carbon atoms.

3. The synthetic monomycolyl glycerol compound according to claim 1, wherein said backbone is partially unsaturated.

4. An immunogenic composition comprising
   (a) a synthetic monomycolyl glycerol compound according to claim 1; and
   (b) an antigenic component.

5. The immunogenic composition according to claim 4, wherein said synthetic monomycolyl glycerol compound is 3-hydroxy-2-ethyl-hexanoic acid-2,3-dihydroxypropyl ester or 3-hydroxy-2-hexyl-decanoic acid-2,3-dihydroxypropyl ester.

6. An adjuvanting or immunomodulating composition comprising a synthetic monomycolyl glycerol compound comprising a backbone, said backbone consisting of 8 to 36 carbon atoms, and a glycerol group.

7. The adjuvanting or immunomodulating composition according to claim 6, further comprising monophosphoryl lipid A (MPL), polyinosinic polycytidylic acid (poly-IC), muramyl dipeptide (MDP), zymosan, double stranded RNA (dsRNA), DC-Chol, CpG oligodeoxynucleotides, cationic peptides, TLR agonists, TLR antagonists, trehalose 6,6'-dimycolate (TDM), alpha,alpha'-trehalose 6,6'-dibehenate (TDB), or tamoxifen.

8. A vaccine comprising an adjuvanting or immunomodulating composition according to claim 6 and an antigenic component, said antigenic component comprising an antigenic epitope.

9. The vaccine according to claim 8, formulated for parenteral administration.

10. A delivery system comprising an adjuvanting or immunomodulating composition according to claim 6 for treating cancer, an autoimmune disorder, a nerve disorder, an inflammatory disorder, infectious disease, a skin disorder, an allergy, asthma, or a disease caused by a pathogen.

11. The delivery system according to claim 10, wherein said adjuvanting or immunomodulating composition further comprises one or more vaccines, antigens, antibodies, cytotoxic agents, allergens, antibiotics, antisense oligonucleotides, agonists, peptides, proteins, gene therapy vectors, or DNA vaccines.

12. An adjuvanting or immunomodulating composition according to claim 6, said composition further comprising a carrier or excipient.

13. The adjuvanting or immunomodulating composition according to claim 6, further comprising a surfactant.

14. The adjuvanting or immunomodulating composition according to claim 13, wherein the surfactant comprises dimethyldioactadecylammonium bromide (DDA-B), dimethyldioactadecylammonium chloride (DDA-C), dimethyldioactadecylammonium sulfate, dimethyldioactadecylammonium phosphate, dimethyldioactadecylammonium acetate, dimethyldioctadecenylammonium bromide (DODA-B), dimethyldioctadecenylammonium chloride (DODA-C), dimethyldioctadecenylammonium sulfate, dimethyldioctadecenylammonium phosphate, dimethyldioctadecenylammonium acetate, 1,2-dioleoyl-3-trimethylammonium propane (DOTAP), 1,2-dimyristol-3-trimethylammonium-propane (DODAP), N-[1-(2,3-dioleyloxy)propyl]-N,N,N-trimethylammonium (DOTMA), dipalmitoylphosphatidylcholine (DPPC), distearoylphosphatidylcholine (DSPC), diarachidonylphosphatidylcholine (DAPC), dipalmitoylphosphatidylethanolamine (DPPE), distearoylphosphatidylethanolamine (DSPE), diarachidoylphosphatidylethanolamine (DAPE), dipalmitoyl-phosphatidylglycerol (DPPG), distearoylphosphatidylglycerol (DSPG), or diarachidoylphosphatidylglycerol (DAPG).

15. The vaccine according to claim 8, wherein said antigenic epitope is from an intracellular pathogen.

16. The vaccine according to claim 15, wherein said antigenic epitope is from a virulent mycobacterium.

17. The vaccine according to claim 15, wherein said antigenic epitope is from *Plasmodium falciparum, Chlamydia trachomatis*, HIV, influenzae, Hepatitis B or Hepatitis C.

18. The vaccine according to claim 16, wherein said virulent mycobacterium is *Mycobacterium tuberculosis, M. bovis*, or *M. africanum*.

19. The vaccine according to claim 8 for treating cancer, an autoimmune disorder, a nerve disorder, an inflammatory disorder, infectious disease, a skin disorder, an allergy, asthma, or a disease caused by a pathogen.

20. The vaccine according to claim 18, wherein said antigenic component is Ag85b_TB10.4, Ag85b_ESAT-6_Rv2660, Ag85b_TB10.4Rv2660 or Ag85a_TB10.4_Rv2660.

* * * * *

UNITED STATES PATENT AND TRADEMARK OFFICE
CERTIFICATE OF CORRECTION

PATENT NO. : 8,563,009 B2  
APPLICATION NO. : 12/666102  
DATED : October 22, 2013  
INVENTOR(S) : Else Marie Agger et al.

Page 1 of 1

It is certified that error appears in the above-identified patent and that said Letters Patent is hereby corrected as shown below:

In the Claims:

Claim 11, fifth line (column 22, line 5), delete the term "agonists".

Claim 20, third line (column 22, line 49), replace "Ag85B_TB10.4Rv2660" with --Ag85B_TB10.4_Rv2660--.

Signed and Sealed this
Thirty-first Day of December, 2013

Margaret A. Focarino
*Commissioner for Patents of the United States Patent and Trademark Office*

UNITED STATES PATENT AND TRADEMARK OFFICE
CERTIFICATE OF CORRECTION

Page 1 of 1

PATENT NO. : 8,563,009 B2
APPLICATION NO. : 12/666102
DATED : October 22, 2013
INVENTOR(S) : Agger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 651 days.

Signed and Sealed this
Third Day of March, 2015

Michelle K. Lee
*Deputy Director of the United States Patent and Trademark Office*